(12) United States Patent
Frost et al.

(10) Patent No.: US 6,432,979 B1
(45) Date of Patent: Aug. 13, 2002

(54) METHOD OF TREATING OR INHIBITING COLONIC POLYPS AND COLORECTAL CANCER

(75) Inventors: Philip Frost, Morris Township, NJ (US); Carolyn M. Discafani-Marro, Cortlandt Manor, NY (US)

(73) Assignee: American Cyanamid Company, Madison, NJ (US)

( * ) Notice: Subject to any disclaimer, the term of this patent is extended or adjusted under 35 U.S.C. 154(b) by 0 days.

(21) Appl. No.: 09/634,787

(22) Filed: Aug. 9, 2000

Related U.S. Application Data

(60) Provisional application No. 60/198,212, filed on Aug. 12, 1999, now abandoned.

(51) Int. Cl.$^7$ .......................... A61K 31/47; A61K 31/19
(52) U.S. Cl. .................. 514/313; 514/312; 514/314; 514/569
(58) Field of Search ................. 514/312, 313, 514/569, 314

(56) References Cited

U.S. PATENT DOCUMENTS

| | | | |
|---|---|---|---|
| 5,480,833 A | 1/1996 | Kikkawa et al. | |
| 5,736,534 A | 4/1998 | Arnold | |
| 5,747,498 A | 5/1998 | Schnur et al. | |
| 5,760,041 A | 6/1998 | Wissner et al. | |
| 6,002,008 A | * 12/1999 | Wissner et al. | 514/312 |
| 6,096,749 A | 8/2000 | Traxler et al. | |
| 6,231,888 B1 | * 5/2001 | Lerner et al. | 514/449 |

FOREIGN PATENT DOCUMENTS

| | | |
|---|---|---|
| EP | 0520722 | 12/1992 |
| EP | 0566226 | 10/1993 |
| EP | 0602851 | 12/1993 |
| EP | 0614661 | 9/1994 |
| EP | 0635498 | 1/1995 |
| EP | 0635507 | 1/1995 |
| WO | 9515758 | 6/1995 |
| WO | 9515781 | 6/1995 |
| WO | 9519774 | 7/1995 |
| WO | 9519970 | 7/1995 |
| WO | 9521613 | 8/1995 |
| WO | 9523141 | 8/1995 |
| WO | 9524190 | 9/1995 |
| WO | 9609294 | 3/1996 |
| WO | 9628148 | 9/1996 |
| WO | 9633977 | 10/1996 |
| WO | 9633978 | 10/1996 |
| WO | 9633979 | 10/1996 |
| WO | 9633980 | 10/1996 |
| WO | 9633981 | 10/1996 |
| WO | 9640142 | 12/1996 |
| WO | 9719065 | 5/1997 |
| WO | 9738983 | 10/1997 |
| WO | 9802434 | 1/1998 |
| WO | 9802438 | 1/1998 |
| WO | 9811095 | 3/1998 |
| WO | 9813350 | 4/1998 |
| WO | 9818782 | 5/1998 |
| WO | 9841525 | 9/1998 |
| WO | 9907701 | 2/1999 |
| WO | 9910325 | 3/1999 |
| WO | WO 9923077 | 5/1999 |
| WO | WO 99 24037 A | 5/1999 |
| WO | 0018761 | 4/2000 |

OTHER PUBLICATIONS

Kelloff, et al, "New Agents for Cancer Chemoprevention", J. Cell. Biochem. 1997, vol. 1996, (suppl. 26), 1–28.

* cited by examiner

*Primary Examiner*—Jerome D. Goldberg
(74) *Attorney, Agent, or Firm*—John W. Hogan, Jr.

(57) ABSTRACT

This invention provides a method of treating or inhibiting colonic polyps or treating or inhibiting colorectal cancer in a mammal in need thereof which comprises administering to said mammal an NSAID and an EFGR kinase inhibitor.

7 Claims, No Drawings

METHOD OF TREATING OR INHIBITING COLONIC POLYPS AND COLORECTAL CANCER

This application claims the benefit of U.S. Provisional Application No. 60/198,212, which was converted from U.S. patent application Ser. No. 09/373,261, filed Aug. 12, 1999 now abandoned, pursuant to a petition filed under 37 C.F.R. 1.53(c)(2)(i).

This invention relates to the use of a combination of an NSAID and a epidermal growth factor receptor (EGFR) kinase inhibitor in the treatment and inhibition of colonic polyps and colorectal cancer.

Colonic Polyps occur in both a familial pattern (familial adenomatous polyps; FAP) and sporadically. FAP afflicts approximately 25,000 patients in the US; while it is estimated that sporadic adenomatous polyps (SAP) occur in approximately 2 million people per year in the US alone. All these patients are at risk for developing adenocarcinoma of the colon. In the case of FAP, that risk is virtually 100% and these patients usually undergo a colectomy at an early age. Patients with sporadic polyps are treated with polypectomy and require periodic colonoscopic examination because of their inherent risk of developing recurrent polyps. In fact, parents and siblings of these patients are also at increased risk for developing colorectal cancer.

The genetic basis for FAP has been linked to the presence of mutations in the APC gene. Similar APC mutations have been found in patients with sporadic polyps. Biochemically, the APC mutation occurs in conjunction with the increased expression of cyclooxygenase enzymes, particularly COX-2. These enzymes are essential for the production of prostenoids, (prostaglandin's; (PG's)) that mediate a number of functions in the bowel including motility, vascular tone, angiogenesis and mucosal protection. PG's are also purported to discourage apoptosis and this is proposed as an explanation for polyp formation.

The therapy of FAP and SAP has focused on inhibiting COX enzymes. Considerable evidence exists for the efficacy of COX inhibitors in reducing polyp formation. These COX inhibitors are predominantly NSAID's such as clinoril, sulindac, piroxicam and etodoloc, all of which appear to be equivalent in their action. A major problem with NSAID therapy has been the development of serious side effects including peptic ulceration, and cholestatic hepatitis and renal papillary necrosis. Long term therapy with NSAIDs for the treatment of polyps is therefore considered to be impractical.

Protein tyrosine kinases are a class of enzymes that catalyze the transfer of a phosphate group from ATP or GTP to tyrosine residue located on protein substrates. Protein tyrosine kinases clearly play a role in normal cell growth. Many of the growth factor receptor proteins function as tyrosine kinases and it is by this process that they effect signaling. The interaction of growth factors with these receptors is a necessary event in normal regulation of cell growth. However, under certain conditions, as a result of either mutation or overexpression, these receptors can become deregulated; the result of which is uncontrolled cell proliferation which can lead to tumor growth and ultimately to the disease known as cancer [Wilks A. F., *Adv. Cancer Res.*, 60, 43 (1993) and Parsons, J. T.; Parsons, S. J., *Important Advances in Oncology,* DeVita V. T. Ed., J.B. Lippincott Co., Phila., 3 (1993)]. Among the growth factor receptor kinases and their proto-oncogenes that have been identified and which are targets of the compounds of this invention are the epidermal growth factor receptor kinase (EGF-R kinase, the protein product of the erbB oncogene), and the product produced by the erbB-2 (also referred to as the neu or HER2) oncogene. Since the phosphorylation event is a necessary signal for cell division to occur and since overexpressed or mutated kinases have been associated with cancer, an inhibitor of this event, a protein tyrosine kinase inhibitor, will have therapeutic value for the treatment of cancer and other diseases characterized by uncontrolled or abnormal cell growth. For example, overexpression of the receptor kinase product of the erbB-2 oncogene has been associated with human breast and ovarian cancers [Slamon, D. J., et. al., *Science,* 244, 707 (1989) and *Science,* 235, 1146 (1987)]. Deregulation of EGF-R kinase has been associated with epidermoid tumors [Reiss, M., et. al., *Cancer Res.,* 51, 6254 (1991)], breast tumors [Macias, A., et. al., *Anticancer Res.,* 7, 459 (1987)], and tumors involving other major organs [Gullick, W. J., *Brit. Med. Bull.,* 47, 87 (1991)]. Because of the importance of the role played by deregulated receptor kinases in the pathogenesis of cancer, many recent studies have dealt with the development of specific PTK inhibitors as potential anti-cancer therapeutic agents [some recent reviews: Burke. T. R., *Drugs Future,* 17, 119 (1992) and Chang, C. J.; Geahlen, R. L., *J. Nat. Prod.,* 55, 1529 (1992)].

It has recently been proposed that the activation and overexpression of COX-2 in adenomatous polyps is due to activation of the EGFR. EGFR stimulation by one of it's ligands—amphiregulin (AR), induces the nuclear targeting of COX-2, release of PG's and subsequent mitogenesis, in polarized colonic epithelial cells. COX-2 inhibitors have been shown to prevent this series of events.

Colon cancer results from an accumulation of a number of genetic abnormalities that occur over the lifetime of the developing tumor. The primary genetic change is a mutation in a gene called APC and this gene mutation occurs prior to the development of adenomas. Subsequent changes include mutations in the K-Ras, DCC and P53 genes as well as other changes that have not as yet been defined. What is known is that there is a clear progression from dysplastic cells within the colon through early adenomas (polyps) to intermediate adenomas, late adenomas to carcinoma and its metastases.

There are a number of diseases that begin as polyps and progress to cancer. The best defined of these is FAP (familial adenomatous polyposis) which has a population incidence of 1 in 7,000. The APC mutation, or a mutation in a gene associated with the function of APC, occurs in close to 100% of these patients. A similar occurrence of the APC mutation is present in sporadic adenomas and sporadic cancers. These adenomas occur with a population and incidence of 1 and 20.

DESCRIPTION OF THE INVENTION

This invention provides a method of treating or inhibiting colonic polyps or colorectal cancer in a mammal in need thereof, which comprises administering to said mammal an NSAID (including COX-1 and/or COX-2 inhibitors) and an EGFR kinase inhibitor.

The chemical structures of NSAIDs vary. Certain NSAIDs, such as ketoprofen, fluribiorifen are aryl propionic acids, while others are cyclized derivatives of arylpropionic acids, arylacetic acids, thiazinecarboxamides, and the like. Preferred NSAIDs include, but are not limited to, ibuprofen, sulindac, ketoporfen, fenoprofen, flurbiprofen, naproxen, tiaprofenic acid, suprofen, etodolac, carprofen, ketrolac, piprofen, indoprofen, celecoxib, rofecoxib, mobicox, and benoxaprofen. The NSAIDs of this invention are either commercially available or can be prepared by standard literature procedures.

For the purpose of defining the scope of this invention, an EGFR kinase inhibitor is defined as a molecule which inhibits the kinase domain of the EGFR. Compounds which are EGFR kinase inhibitors can readily be identified by one skilled in the art using numerous methods, including the following standard pharmacological test procedure which measures the inhibition of the phosphorylation of the tyrosine residue of a peptide substrate catalyzed by EGFR kinase. Briefly, the peptide substrate (RR-SRC) has the sequence arg-arg-leu-ile-glu-asp-ala-glu-tyr-ala-ala-arg-gly. The enzyme is obtained as a membrane extract of A431 cells (American Type Culture Collection, Rockville, Md.). A431 cells are grown in T175 flasks to 80% confluency. The cells are washed twice with phosphate buffered saline (PBS) without $Ca^{2+}$. Flasks are rotated for 1.5 hours in 20 ml PBS with 1.0 mM ethylenediaminetetraacetic acid (EDTA) at room temperature and centrifuged at 600 g for 10 minutes. The cells are solubilized in 1 ml per $5 \times 10^6$ cells of cold lysis buffer {10 mM 4-(2-hydroxyethyl)-1-piperazineethanesulfonic acid (HEPES), pH 7.6, 10 mM NaCl, 2 mM EDTA, 1 mM phenylmethylsulfonyl-fluoride (PMSF), 10 mg/ml aprotinin, 10 mg/ml leupeptin, 0.1 mM sodium orthovanadate} in a Dounce homogenizer with 10 strokes on ice. The lysate is centrifuged at 600 g for 10 minutes first to clear cell debris and the supernatant further centrifuged at 100,000 g for 30 min at 4° C. The membrane pellet is suspended in 1.5 ml HNG buffer (50 mM HEPES, pH 7.6, 125 mM NaCl, 10% glycerol). The membrane extract is divided into aliquots, immediately frozen in liquid nitrogen and stored at −70° C.

Compounds to be evaluated are made into 10 mg/ml stock solutions in 100% dimethylsulfoxide (DMSO). Prior to experiment, stock solutions are diluted to 500 mM with buffer (30 mM Hepes pH 7.4) and then serially diluted to the desired concentration.

An aliquot of the A431 membrane extract (10 mg/ml) is diluted in 30 mM HEPES (pH 7.4) to give a protein concentration of 50 ug/ml. To 4 μl of enzyme preparation, EGF (1 μl at 12 μg/ml) is added and incubated for 10 min on ice followed by 4 μl of the test compound or buffer; this mix is incubated on ice for 30 min. To this is added the $^{33}$P-ATP (10 mCi/ml) diluted 1:10 in assay buffer along with the substrate peptide at a concentration of 0.5 mM (control reactions get no test compound) and the reaction is allowed to proceed for 30 min at 30° C. The reaction is stopped with 10% TCA and left on ice for at least 10 min after which tubes are microcentrifuged at full speed for 15 min. Then a portion of the supernatants are spotted on P81 phosphocellulose discs and washed twice in 1% acetic acid then water for 5 min each followed by scintillation counting. The results obtained can be expressed as an $IC_{50}$. The $IC_{50}$ is the concentration of test compound needed to reduce the total amount of phosphorylated substrate by 50%. The % inhibition of the test compound is determined for at least three different concentrations and the $IC_{50}$ value is evaluated from the dose response curve. The % inhibition is evaluated with the following formula:

$$\% \text{ inhibition} = 100 - [\text{CPM(drug)}/\text{CPM(control)}] \times 100$$

where CPM(drug) is in units of counts per minute and is a number expressing the amount of radiolabeled ATP (g-$^{33}$P) incorporated onto the RR-SRC peptide substrate by the enzyme after 30 minutes at 30° C. in the presence of test compound as measured by liquid scintillation counting. CPM(control) is in units of counts per minute and is a number expressing the amount of radiolabeled ATP (g-$^{33}$P) incorporated into the RR-SRC peptide substrate by the enzyme after 30 minutes at 30° C. in the absence of test compound as measured by liquid scintillation counting. The CPM values are corrected for the background counts produced by ATP in the absence of the enzymatic reaction. Compounds having an $IC_{50}$ of 200 nM or less are considered to be significantly active EGFR kinase inhibitors.

It is preferred that the EGFR kinase inhibitor irreversibly inhibits EGFR kinase, typically by possessing a reactive moiety (such as a Michael acceptor) which can form a covalent bond with EGFR.

More preferred EGFR kinase inhibitors include the following:

A. Quinazolines of Formula 1, which are disclosed in U.S. Pat. No. 5,760,041, and PCT Patent Application Publication WO 99/09016. These compounds can be prepared according to the methodology described in U.S. Pat. No. 5,760,041, which is hereby incorporated by reference. The structure of the EGFR kinase inhibitors of Formula 1 are as follows:

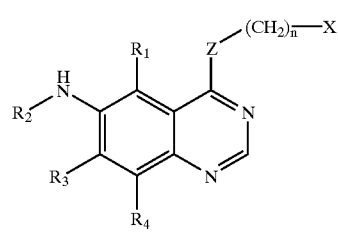

wherein
  X is cycloalkyl of 3 to 7 carbon atoms, which may be optionally substituted with one or more alkyl of 1 to 6 carbon atom groups; or is a pyridinyl, pyrimidinyl, or phenyl ring wherein the pyridinyl, pyrimidinyl, or phenyl ring may be optionally mono- di-, or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalky of 3–8 carbon atoms, aminomethyl, N-alkylaminomethyl of 2–7 carbon atoms, N,N-dialkylaminomethyl of 3–7 carbon atoms, mercapto, methylmercapto, and benzoylamino;
  Z is —NH—, —O—, —S—, or —NR—;
  R is alkyl of 1–6 carbon atoms, or carboalkyl of 2–7 carbon atoms;
  $R_1$, $R_3$, and $R_4$ are each, independently, hydrogen, halogen, alkyl of 1–6 carbon atoms, alkenyl of 2–6 carbon atoms, alkenyloxy of 2–6 carbon atoms, alkynyloxy of 2–6 carbon atoms, hydroxymethyl, halomethyl, alkanoyloxy of 1–6 carbon atoms, alkenoyloxy of 3–8 carbon atoms, alkynoyloxy of 3–8 carbon atoms, alkanoyloxymethyl of 2–7 carbon atoms, alkenoyloxymethyl of 4–9 carbon atoms, alkynoyloxymethyl of 4–9 carbon atoms, alkoxymethyl of 2–7 carbon atoms, alkoxy of 1–6 carbon atoms, alkylthio of 1–6 carbon atoms, alkylsulphinyl of 1–6 carbon atoms, alkylsulphonyl of 1–6 carbon atoms, alkylsulfonamido of 1–6 carbon atoms, alkenylsulfonamido of 2–6 carbon atoms, alkynylsulfonamido of 2–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzyl, amino, hydroxyamino, alkoxyamino of 1–4 carbon atoms, alkylamino of 1–6 carbon atoms, dialkylamino of 2 to 12 carbon atoms, N-alkylcarbamoyl, N,N-dialkylcarbamoyl, N-alkyl-N-alkenylamino of 4 to 12 carbon atoms, N,N-dialkenylamino of 6–12 carbon atoms, phenylamino, benzylamino, $R_7$—$(C(R_6)_2)_g$—Y—, $R_7$—$(C(R_6)_2)_p$—M—$(C(R_6)_2)_k$—Y—, or Het—W—$(C(R_6)_2)_k$—Y—

Y is a divalent radical selected from the group consisting of

—$(CH_2)_a$—, —O—, and

—N—;
 |
 $R_6$ $R_7$ is —$NR_6R_6$, or —$OR_6$;

M is >$NR_6$, —O—, >N—$(C(R_6)_2)_p NR_6R_6$, or >N—$(C(R_6)_2)_p$—$OR_6$;

W is >$NR_6$, —O— or is a bond;

Het is a heterocycle, optionally mono- or di-substituted on carbon or nitrogen with $R_6$ and optionally mono-substituted on carbon with —$CH_2OR_6$; wherein the heterocycle is selected from the group consisting of morpholine, thiomorpholine, thiomorpholine S-oxide, thiomorpholine S,S-dioxide, piperidine, pyrrolidine, aziridine, imidazole, 1,2,3-triazole, 1,2,4-triazole, tetrazole, piperazine, tetrahydrofuran, and tetrahydropyran;

$R_6$ is hydrogen, alkyl of 1–6 carbon atoms, alkenyl of 2–6 carbon atoms, alkynyl of 2–6 carbon atoms, cycloalkyl of 1–6 carbon atoms, carboalkyl of 2–7 carbon atoms, carboxyalkyl (2–7 carbon atoms), phenyl, or phenyl optionally substituted with one or more halogen, alkoxy of 1–6 carbon atoms, trifluoromethyl, amino, alkylamino of 1–3 carbon atoms, dialkylamino of 2–6 carbon atoms, nitro, cyano, azido, halomethyl, alkoxymethyl of 2–7 carbon atoms, alkanoyloxymethyl of 2–7 carbon atoms, alkylthio of 1–6 carbon atoms, hydroxy, carboxyl, carboalkoxy of 2–7 carbon atoms, phenoxy, phenyl, thiophenoxy, benzoyl, benzyl, phenylamino, benzylamino, alkanoylamino of 1–6 carbon atoms, or alkyl of 1–6 carbon atoms;

$R_2$, is selected from the group consisting of

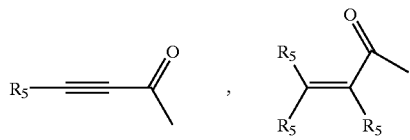

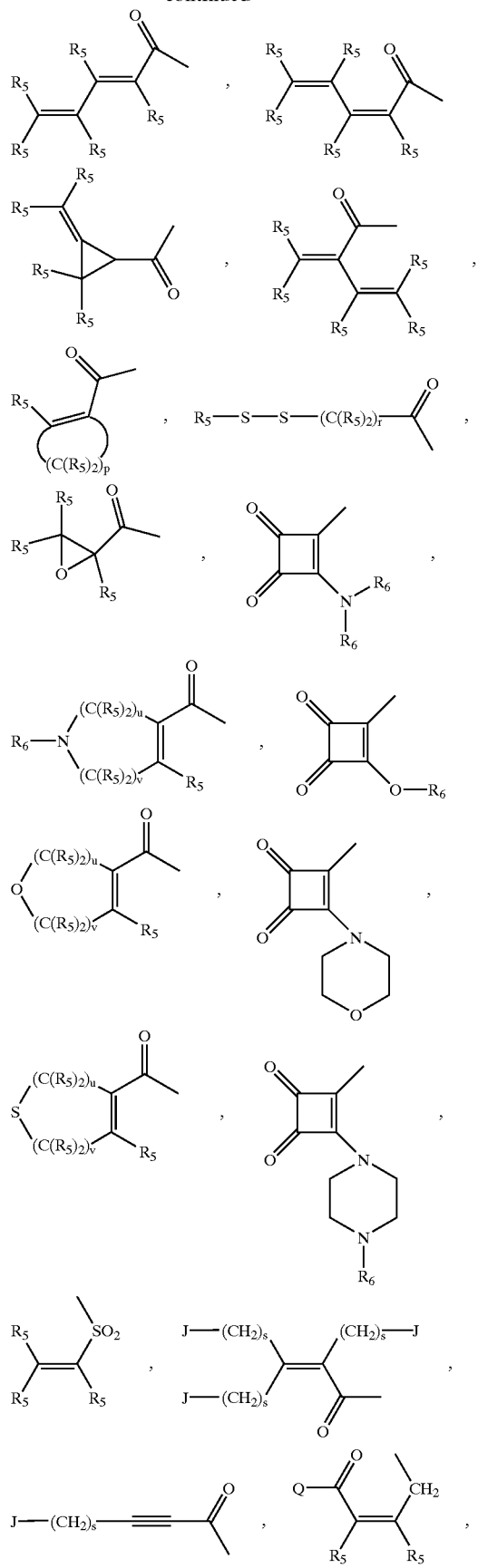

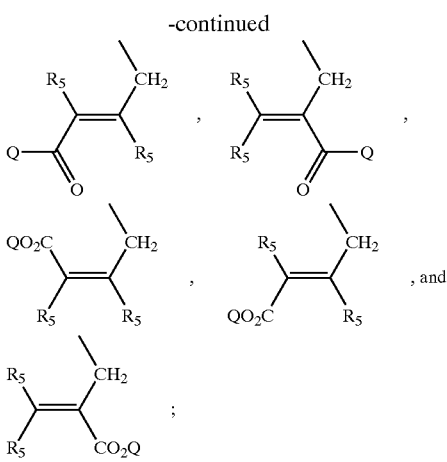

$R_5$ is independently hydrogen, alkyl of 1–6 carbon atoms, carboxy, carboalkoxy of 1–6 carbon atoms, phenyl, carboalkyl of 2–7 carbon atoms, $R_7—(C(R_6)_2)_s—$, $R_7—(C(R_6)_2)_p—M—(C(R_6)_2)_r—$, $R_8R_9—CH—M—(C(R_6)_2)_r—$, or $Het—W—(C(R_6)_2)_r—$;

$R_8$, and $R_9$ are each, independently, $—(C(R_6)_2)_rNR_6R_6$, or $—(C(R_6)_2)_rOR_6$;

J is independently hydrogen, chlorine, fluorine, or bromine;

Q is alkyl of 1–6 carbon atoms or hydrogen;

a=0 or 1;
g=1–6;
k=0–4;
n is 0–1;
p=2–4;
q=0–4;
r=1–4;
s=1–6;
u=0–4 and v=0–4, wherein the sum of u+v is 2–4;

or a pharmaceutically acceptable salt thereof.

With respect to the quinazolines of Formula 1, The pharmaceutically acceptable salts are those derived from such organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

The alkyl portion of the alkyl, alkoxy, alkanoyloxy, alkoxymethyl, alkanoyloxymethyl, alkylsulphinyl, alkylsulphonyl, alkylsulfonamido, carboalkoxy, carboalkyl, carboxyalkyl, carboalkoxyalkyl, alkanoylamino, N-alkylcarbamoyl, and N,N-dialkylcarbamoyl substituents include both straight chain as well as branched carbon chains. The alkenyl portion of the alkenyl, alkenoyloxymethyl, alkenyloxy, alkenylsulfonamido, substituents include both straight chain as well as branched carbon chains and one or more sites of unsaturation. The alkynyl portion of the alkynyl, alkynoyloxymethyl, alkynylsulfonamido, alkynyloxy, substituents include both straight chain as well as branched carbon chains and one or more sites of unsaturation. Carboxy is defined as a $—CO_2H$ radical. Carboalkoxy of 2–7 carbon atoms is defined as a $—CO_2R''$ radical, where R'' is an alkyl radical of 1–6 carbon atoms. Carboxyalkyl is defined as a $HO_2C—R'''—$ radical where R''' is a divalent alkyl radical of 1–6 carbon atoms. Carboalkoxyalkyl is defined as a $R''O_2C—R'''—$ radical where R''' is a divalent akyl radical and where R'' and R''' together have 2–7 carbon atoms. Carboalkyl is defined as a $—COR''$ radical, where R'' is an alkyl radical of 1–6 carbon atoms. Alkanoyloxy is defined as a $—OCOR''$ radical, where R'' is an alkyl radical of 1–6 carbon atoms. Alkanoyloxymethyl is defined as $R''CO_2CH_2—$ radical, where R'' is an alkyl radical of 1–6 carbon atoms. Alkoxymethyl is defined as $R''OCH_2—$ radical, where R'' is an alkyl radical of 1–6 carbon atoms. Alkylsulphinyl is defined as $R''SO—$ radical, where R'' is an alkyl radical of 1–6 carbon atoms. Alkylsulphonyl is defined as $R''SO_2—$ radical, where R'' is an alkyl radical of 1–6 carbon atoms. Alkylsulfonamido, alkenylsulfonamido, alkynylsulfonamido are defined as $R''SO2NH—$ radical, where R'' is an alkyl radical of 1–6 carbon atoms, an alkenyl radical of 2–6 carbon atoms, or an alkynyl radical of 2–6 carbon atoms, respectively. N-alkylcarbamoyl is defined as $R''NHCO—$ radical, where R'' is an alkyl radical of 1–6 carbon atoms. N,N-dialkylcarbamoyl is defined as $R''R'NCO—$ radical, where R'' is an alkyl radical of 1–6 carbon atoms, R' is an alkyl radical of 1–6 carbon atoms and R', and R'' may be the same or different. When X is substituted, it is preferred that it is mono-, di-, or tri-substituted, with monosubstituted being most preferred. It is preferred that of the substituents R1, R3, and R4, at least one is hydrogen and it is most preferred that two or three be hydrogen. It is also preferred that X is a phenyl ring, Z is $—NH—$, and n=0.

Het is a heterocycle, as defined above which may be optionally mono- or di-substituted with $R_6$ on carbon or nitrogen and optionally mono-substituted on carbon with $—CH_2OR_6$. Het may be bonded to W via a carbon atom on the heterocyclic ring, or when Het is a nitrogen containing heterocycle which also contains a saturated carbon-nitrogen bond, such heterocycle may be bonded to W, via the nitrogen when W is a bond. When Het is substituted with $R_6$, such substitution may be on a ring carbon, or in the case of a nitrogen containing heterocycle, which also contains a saturated carbon-nitrogen, such nitrogen may be substituted with $R_6$. Preferred substituted heterocycles include 2,6-disubstituted morpholine, 2,5-disubstituted thiomorpholine, 2-substituted imidazole, N-subsitituted 1,4-piperazine, N-subsitituted piperadine, and N-substituted pyrrolidine.

The compounds of Formula 1 may contain one or more asymmetric carbons atoms; in such cases, the compounds of Formula 1 cover the individual diasteromers, the racemates, and the individual R and S entantiomers thereof.

B. Cyanoquinolines of Formula 2, which are disclosed in U.S. Pat. No. 6,002,008, and PCT Patent Application Publication WO 98/43960. These compounds can be prepared according to the methodology described in U.S. Pat. No. 6,002,008 which is hereby incorporated by reference. The structure of the EGFR kinase inhibitors of Formula 2 are as follows:

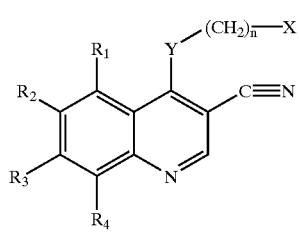

2 wherein:
    X is cycloalkyl of 3 to 7 carbon atoms, which may be optionally substituted with one or more alkyl of 1 to 6 carbon atom groups; or is a pyridinyl, pyrimidinyl, or phenyl ring; wherein the pyridinyl, pyrimidinyl, or phenyl ring may be optionally mono- di-, or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, and benzoylamino;

n is 0–1;

Y is —NH—, —O—, —S—, or —NR—;

R is alkyl of 1–6 carbon atoms;

$R_1$, $R_2$, $R_3$, and $R_4$ are each, independently, hydrogen, halogen, alkyl of 1–6 carbon atoms, alkenyl of 2–6 carbon atoms, alkynyl of 2–6 carbon atoms, alkenyloxy of 2–6 carbon atoms, alkynyloxy of 2–6 carbon atoms, hydroxymethyl, halomethyl, alkanoyloxy of 1–6 carbon atoms, alkenoyloxy of 3–8 carbon atoms, alkynoyloxy of 3–8 carbon atoms, alkanoyloxymethyl of 2–7 carbon atoms, alkenoyloxymethyl of 4–9 carbon atoms, alkynoyloxymethyl of 4–9 carbon atoms, alkoxymethyl of 2–7 carbon atoms, alkoxy of 1–6 carbon atoms, alkylthio of 1–6 carbon atoms, alkylsulphinyl of 1–6 carbon atoms, alkylsulphonyl of 1–6 carbon atoms, alkylsulfonamido of 1–6 carbon atoms, alkenylsulfonamido of 2–6 carbon atoms, alkynylsulfonamido of 2–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzyl, amino, hydroxyamino, alkoxyamino of 1–4 carbon atoms, alkylamino of 1–6 carbon atoms, dialkylamino of 2 to 12 carbon atoms, aminoalkyl of 1–4 carbon atoms, N-alkylaminoalkyl of 2–7 carbon atoms, N,N-dialkylaminoalkyl of 3–14 carbon atoms, phenylamino, benzylamino,

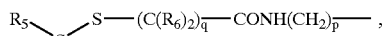

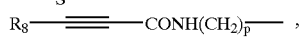

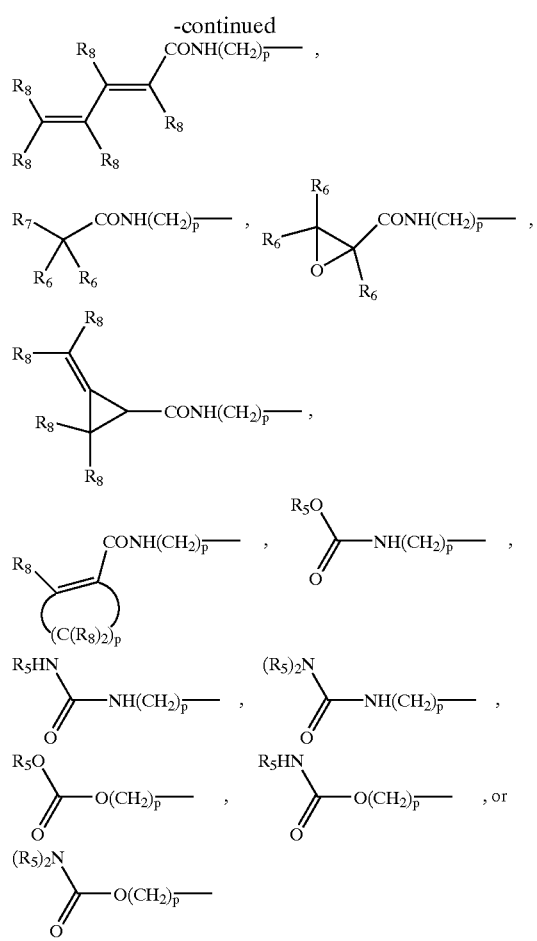

$R_5$ is alkyl of 1–6 carbon atoms, alkyl optionally substituted with one or more halogen atoms, phenyl, or phenyl optionally substituted with one or more halogen, alkoxy of 1–6 carbon atoms, trifluoromethyl, amino, nitro, cyano, or alkyl of 1–6 carbon atoms groups;

$R_6$ is hydrogen, alkyl of 1–6 carbon atoms, or alkenyl of 2–6 carbon atoms;

$R_7$ is chloro or bromo $R_8$ is hydrogen, alkyl of 1–6 carbon atoms, aminoalkyl of 1–6 carbon atoms, N-alkylaminoalkyl of 2–9 carbon atoms, N,N-dialkylaminoalkyl of 3–12 carbon atoms, N-cycloalkylaminoalkyl of 4–12 carbon atoms, N-cycloalkyl-N-alkylaminoalkyl of 5–18 carbon atoms, N,N-dicycloalkylaminoalkyl of 7–18 carbon atoms, morpholino-N-alkyl wherein the alkyl group is 1–6 carbon atoms, piperidino-N-alkyl wherein the alkyl group is 1–6 carbon atoms, N-alkyl-piperidino-N-alkyl wherein either alkyl group is 1–6 carbon atoms, azacycloalkyl-N-alkyl of 3–11 carbon atoms, hydroxyalkyl of 1–6 carbon atoms, alkoxyalkyl of 2–8 carbon atoms, carboxy, carboalkoxy of 1–6 carbon atoms, phenyl, carboalkyl of 2–7 carbon atoms, chloro, fluoro, or bromo;

Z is amino, hydroxy, alkoxy of 1–6 carbon atoms, alkylamino wherein the alkyl moiety is of 1–6 carbon atoms, dialkylamino wherein each of the alkyl moieties is of 1–6 carbon atoms, morpholino, piperazino, N-alkylpiperazino wherein the alkyl moiety is of 1–6 carbon atoms, or pyrrolidino;

m=1–4, q=1–3, and p=0–3;

any of the substituents $R_1$, $R_2$, $R_3$, or $R_4$ that are located on contiguous carbon atoms can together be the divalent radical —O—C($R_8$)$_2$—O—;

or a pharmaceutically acceptable salt thereof with the proviso that when Y is —NH—, $R_1$, $R_2$, $R_3$, and $R_4$ are hydrogen, and n is 0, X is not 2-methylphenyl.

With respect to the cyanoquilines of Formula 2, the pharmaceutically acceptable salts are those derived from such organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

The alkyl portion of the alkyl, alkoxy, alkanoyloxy, alkoxymethyl, alkanoyloxymethyl, alkylsulphinyl, alkylsulphonyl, alkylsulfonamido, carboalkoxy, carboalkyl, alkanoylamino aminoalkyl, alkylaminoalkyl, N,N-dicycloalkylaminoalkyl, hydroxyalkyl, and alkoxyalkyl substituents include both straight chain as well as branched carbon chains. The cycloalkyl portions of N-cycloalkyl-N-alkylaminoalkyl and N,N-dicycloalkylaminoalkyl substituents include both simple carbocycles as well as carbocycles containing alkyl substituents. The alkenyl portion of the alkenyl, alkenoyloxymethyl, alkenyloxy, alkenylsulfonamido, substituents include both straight chain as well as branched carbon chains and one or more sites of unsaturation. The alkynyl portion of the alkynyl, alkynoyloxymethyl, alkynylsulfonamido, alkynyloxy, substituents include both straight chain as well as branched carbon chains and one or more sites of unsaturation. Carboxy is defined as a —CO$_2$H radical. Carboalkoxy of 2–7 carbon atoms is defined as a —CO$_2$R" radical, where R" is an alkyl radical of 1–6 carbon atoms. Carboalkyl is defined as a —COR" radical, where R" is an alkyl radical of 1–6 carbon atoms. Alkanoyloxy is defined as a —OCOR" radical, where R" is an alkyl radical of 1–6 carbon atoms. Alkanoyloxymethyl is defined as R"CO$_2$CH$_2$— radical, where R" is an alkyl radical of 1–6 carbon atoms. Alkoxymethyl is defined as R"OCH$_2$— radical, where R" is an alkyl radical of 1–6 carbon atoms. Alkylsulphinyl is defined as R"SO— radical, where R" is an alkyl radical of 1–6 carbon atoms. Alkylsulphonyl is defined as R"SO$_2$— radical, where R" is an alkyl radical of 1–6 carbon atoms. Alkylsulfonamido, alkenylsulfonamido, alkynylsulfonamido are defined as R"SO$_2$NH— radical, where R" is an alkyl radical of 1–6 carbon atoms, an alkenyl radical of 2–6 carbon atoms, or an alkynyl radical of 2–6 carbon atoms, respectively. N-alkylcarbamoyl is defined as R"NHCO— radical, where R" is an alkyl radical of 1–6 carbon atoms. N,N-dialkylcarbamoyl is defined as R" R'NCO— radical, where R" is an alkyl radical of 1–6 carbon atoms, R' is an alkyl radical of 1–6 carbon atoms and R', and R" may be the same or different. When X is substituted, it is preferred that it is mono-, di-, or tri-substituted, with monosubstituted being most preferred. It is preferred that of the substituents $R_1$, $R_2$, $R_3$, and $R_4$, at least one is hydrogen and it is most preferred that two or three be hydrogen. An azacycloalkyl-N-alkyl substituent refers to a monocyclic heterocycle that contains a nitrogen atom on which is substituted a straight or branched chain alkyl radical. A morpholino-N-alkyl substituent is a morpholine ring substituted on the nitrogen atom with a straight or branch chain alkyl radical. A piperidino-N-alkyl substituent is a piperidine ring substituted on one of the nitrogen atoms with a straight or branch chain alkyl radical. A N-alkyl-piperidino-N-alkyl substituent is a piperidine ring substituted on one of the nitrogen atoms with a straight or branched chain alkyl group and on the other nitrogen atom with a straight or branch chain alkyl radical.

The compounds of Formula 2 may contain an asymmetric carbon; in such cases, the compounds of Formula 2 cover the racemate and the individual R and S entantiomers, and in the case were more than one asymmetric carbon exists, the individual diasteromers, their racemates and individual entantiomers.

C. Cyanoquinolines of Formula 3, which are disclosed in U.S. patent application Ser. No. 09/162,802. These compounds can be prepared according to the methodology described in U.S. patent application Ser. No. 09/049,718, and U.S. patent application Ser. No. 09/162,802, which are hereby incorporated by reference. The structure of the EGFR kinase inhibitors of Formula 3 are as follows:

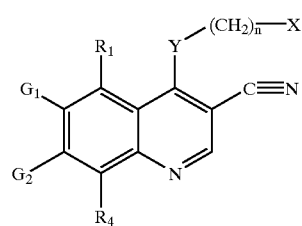

wherein:

X is a bicyclic aryl or bicyclic heteroaryl ring system of 8 to 12 atoms where the bicyclic heteroaryl ring contains 1 to 4 heteroatoms selected from N, O, and S with the proviso that the bicyclic heteroaryl ring does not contain —O—, S—S, or S—O bonds and where the bicyclic aryl or bicyclic heteroaryl ring may be optionally mono- di-, tri, or tetra-substituted with a substituent selected from the group consisting of halogen, oxo, thio, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalky of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 2–9 carbon atoms, N,N-dialkylaminoalkoxy of 3–10 carbon atoms, mercapto, methylmercapto, and benzoylamino; or X is a radical radical having the formula:

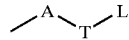

wherein

A is a pyridinyl, pyrimidinyl, or phenyl ring; wherein the pyridinyl, pyrimidinyl, or phenyl ring may be optionally mono- or di-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, is carboalkoxyalky of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 2–9 carbon atoms, N,N-dialkylaminoalkoxy of 3–10 carbon atoms, mercapto, methylmercapto, and benzoylamino;

T is bonded to a carbon of A and is:

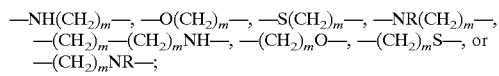

L is an unsubsitituted phenyl ring or a phenyl ring mono-, di-, or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalky of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 2–9 carbon atoms, N,N-dialkylaminoalkoxy of 3–10 carbon atoms, mercapto, methylmercapto, and benzoylamino; provided that L can be an unsubstituted phenyl ring only when m>0 and T is not —$CH_2NH$— or —$CH_2O$—; or L is a 5- or 6-membered heteroaryl ring where the heteroaryl ring contains 1 to 3 heteroatoms selected from N, O, and S, with the proviso that the heteroaryl ring does not contain O—O, S—S, or S—O bonds, and where the heteroaryl ring is optionally mono- or di-substituted with a substituent selected from the group consisting of halogen, oxo, thio, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalky of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 2–9 carbon atoms, N,N-dialkylaminoalkoxy of 3–10 carbon atoms, mercapto, methylmercapto, and benzoylamino;

Z is —NH—, —O—, —S—, or —NR—;

R is alkyl of 1–6 carbon atoms, or carboalkyl of 2–7 carbon atoms;

$G_1$, $G_2$, $R_1$, and $R_4$ are each, independently, hydrogen, halogen, alkyl of 1–6 carbon atoms, alkenyl of 2–6 carbon atoms, alkynyl of 2–6 carbon atoms, alkenyloxy of 2–6 carbon atoms, alkynyloxy of 2–6 carbon atoms, hydroxymethyl, halomethyl, alkanoyloxy of 1–6 carbon atoms, alkenoyloxy of 3–8 carbon atoms, alkynoyloxy of 3–8 carbon atoms, alkanoyloxymethyl of 2–7 carbon atoms, alkenoyloxymethyl of 4–9 carbon atoms, alkynoyloxymethyl of 4–9 carbon atoms, alkoxymethyl of 2–7 carbon atoms, alkoxy of 1–6 carbon atoms, alkylthio of 1–6 carbon atoms, alkylsulphinyl of 1–6 carbon atoms, alkylsulphonyl of 1–6 carbon atoms, alkylsulfonamido of 1–6 carbon atoms, alkenylsulfonamido of 2–6 carbon atoms, alkynylsulfonarnido of 2–6 carbon atoms, hydroxy, trifluoromethyl, trifluoromethoxy, cyano, nitro, carboxy, carboalkoxy of 2–7 carbon atoms, carboalkyl of 2–7 carbon atoms, phenoxy, phenyl, thiophenoxy, benzyl, amino, hydroxyamino, alkoxyamino of 1–4 carbon atoms, alkylamino of 1–6 carbon atoms, dialkylamino of 2 to 12 carbon atoms, N-alkylcarbamoyl, N,N-dialkylcarbamoyl, N-alkyl-N-alkenylamino of 4 to 12 carbon atoms, N,N-dialkenylamino of 6–12 carbon atoms, phenylamino, benzylamino,

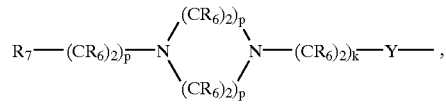

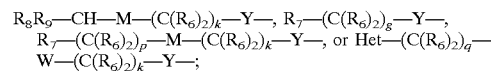

or R1 and R4 are as defined above and $G_1$ or $G_2$ or both are $R_2$—NH—;

or if any of the substituents $R_1$, $G_2$, $G_3$, or $R_4$ are located on contiguous carbon atoms then they may be taken together as the divalent radical —O—$C(R_6)_2$—O—;

Y is a divalent radical selected from the group consisting of

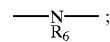

$R_7$ is —$NR_6R_6$, —$OR_6$, —J, —$N(R_6)_3^+$, or —$NR_6(OR_6)$;

M is >$NR_6$, —O—, >N—$(C(R_6)_2)_p NR_6R_6$, or >N—$(C(R_6)_2)_p$—$OR_6$;

W is >$NR_6$, —O— or is a bond;

Het is is selected from the group consisting of morpholine, thiomorpholine, thiomorpholine S-oxide, thiomorpholine S,S-dioxide, piperidine, pyrrolidine, aziridine, pyridine, imidazole, 1,2,3-triazole, 1,2,4-triazole, thiazole, thiazolidine, tetrazole, piperazine, furan, thiophene, tetrahydrothiophene, tetrahydrofuran, dioxane, 1,3-dioxolane, tetrahydropyran, and

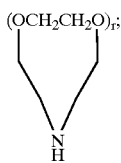

wherein Het is optionally mono- or di-substituted on carbon or nitrogen with $R_6$, optionally mono- or di-substituted on carbon with hydroxy, $-N(R_6)_2$, or $-OR_6$, optionally mono or di-substituted on carbon with the mono-valent radicals $-(C(R_6)_2)_sOR_6$ or $-(C(R_6)_2)_sN(R_6)_2$, and optionally mono or di-substituted on a saturated carbon with divalent radicals $-O-$ or $-O(C(R_6)_2)_sO-$;

$R_6$ is hydrogen, alkyl of 1–6 carbon atoms, alkenyl of 2–6 carbon atoms, alkynyl of 2–6 carbon atoms, cycloalkyl of 1–6 carbon atoms, carboalkyl of 2–7 carbon atoms, carboxyalkyl (2–7 carbon atoms), phenyl, or phenyl optionally substituted with one or more halogen, alkoxy of 1–6 carbon atoms, trifluoromethyl, amino, alkylamino of 1–3 carbon atoms, dialkylamino of 2–6 carbon atoms, nitro, cyano, azido, halomethyl, alkoxymethyl of 2–7 carbon atoms, alkanoyloxymethyl of 2–7 carbon atoms, alkylthio of 1–6 carbon atoms, hydroxy, carboxyl, carboalkoxy of 2–7 carbon atoms, phenoxy, phenyl, thiophenoxy, benzoyl, benzyl, phenylamino, benzylamino, alkanoylamino of 1–6 carbon atoms, or alkyl of 1–6 carbon atoms; with the proviso that the alkenyl or alkynyl moiety is bound to a nitrogen or oxygen atom through a saturated carbon atom;

$R_2$, is selected from the group consisting of

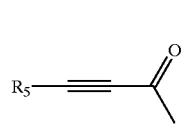 , 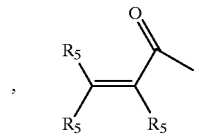 ,

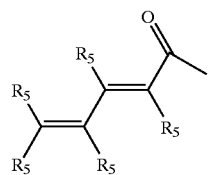 , 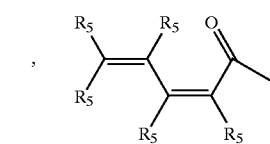 ,

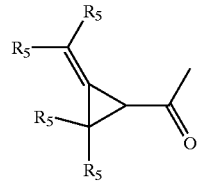 , 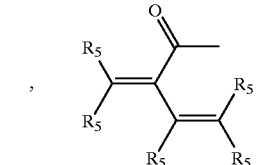 ,

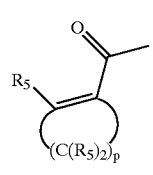 , 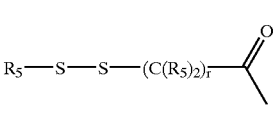 ,

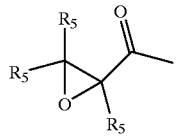 , 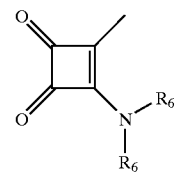 ,

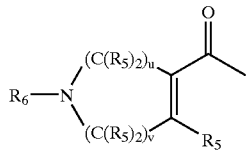 , 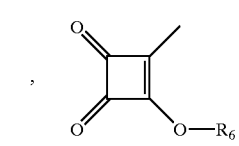 ,

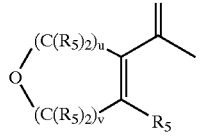 , 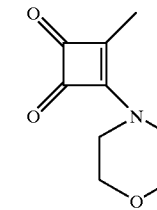 ,

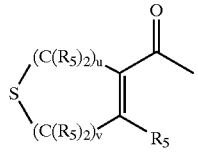 , 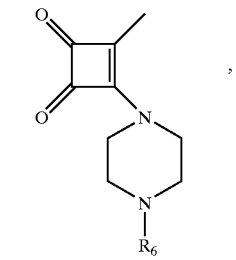 ,

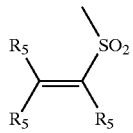 , 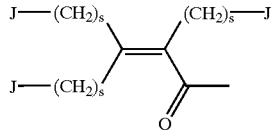 ,

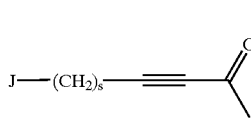 , 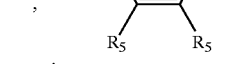 ,

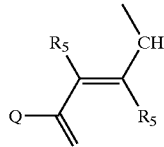 , 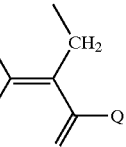 , and

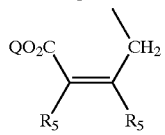 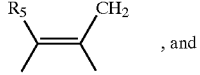

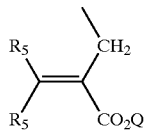 ;

$R_3$ is independently hydrogen, alkyl of 1–6 carbon atoms, carboxy, carboalkoxy of 1–6 carbon atoms, phenyl, carboalkyl of 2–7 carbon atoms,

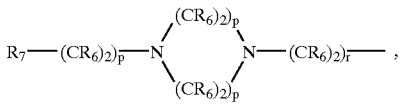

—R$_7$—(C(R$_6$)$_2$)$_s$—, R$_7$—(C(R$_6$)$_2$)$_p$—M—(C(R$_6$)$_2$)$_r$—, R$_8$R$_9$—
CH—M—(C(R$_6$)$_2$)$_r$—, or Het—(C(R$_6$)$_2$)$_q$—W—(C(R$_6$)$_2$)$_r$—;

R$_5$ is independently hydrogen, alkyl of 1–6 carbon atoms, carboxy, carboalkoxy of 1–6 carbon atoms, phenyl, carboalkyl of 2–7 carbon atoms,

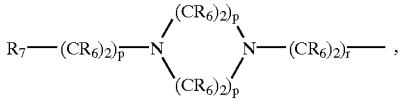

R$_7$—(C(R$_6$)$_2$)$_s$—, R$_7$—(C(R$_6$)$_2$)$_p$—M—(C(R$_6$)$_2$)$_r$—, R$_8$R$_9$—CH—
M—(C(R$_6$)$_2$)$_r$—, or Het—(C(R$_6$)$_2$)$_q$—W—(C(R$_6$)$_2$)$_r$—;

R$_8$, and R$_9$ are each, independently, —(C(R$_6$)$_2$)$_r$NR$_6$R$_6$, or —(C(R$_6$)$_2$)$_r$OR$_6$;

J is independently hydrogen, chlorine, fluorine, or bromine;

Q is alkyl of 1–6 carbon atoms or hydrogen;

a=0 or 1;

g=1–6;

k=0–4;

n is 0–1;

m is 0–3;

p=2–4;

q=0–4;

r=1–4;

s=1–6;

u=0–4 and v=0–4, wherein the sum of u+v is 2–4;

or a pharmaceutically acceptable salt thereof, provided that
when R$_6$ is alkenyl of 2–7 carbon atoms or alkynyl of 2–7 carbon atoms, such alkenyl or alkynyl moiety is bound to a nitrogen or oxygen atom through a saturated carbon atom;

and further provided that
when Y is —NR$_6$— and R$_7$ is —NR$_6$R$_6$, —N(R$_6$)$_3^+$, or —NR$_6$(OR$_6$), then g=2–6;
when M is —O— and R$_7$ is —OR$_6$ then p=1–4;
when Y is —NR$_6$— then k=2–4;
when Y is —O— and M or W is —O— then k=1–4
when W is not a bond with Het bonded through a nitrogen atom then q=2–4 and when W is a bond with Het bonded through a nitrogen atom and Y is —O— or —NR$_6$— then k=2–4.

With respect to the cyanoquinolines of Formula 3, the pharmaceutically acceptable salts are those derived from such organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

Preferred bicyclic aryl or bicyclic heteroaryl ring systems include naphthalene, 1,2,3,4-tetrahydronaphthalene, indane, 1-oxo-indane, 1,2,3,4-tetrahydroquinoline, naphthyridine, benzofuran, 3-oxo-1,3-dihydro-isobenzofuran, benzothiaphene, 1,1-dioxo-benzothiaphene, indole, 2,3-dihydroindole, 1,3-dioxo-2,3-dihydro-1H-isoindole, benzotriazole, 1H-indazole, indoline, benzopyrazole, 1,3-benzodioxole, benzooxazole, purine, phthalimide, coumarin, chromone, quinoline, terahydroquinoline, isoquinoline, benzimidazole, quinazoline, pyrido[2,3-b]pyridine, pyrido[3,4-b]pyrazine, pyrido[3,2-c]pyridazine, pyrido[3,4-b]pyridine, 1H-pyrazole[3,4-d]pyrimidine, 1,4-Benzodioxane, pteridine, 2(1H)-quinolone, 1(2H)-isoquinolone, 2-oxo-2,3-dihydro-benzthiazole, 1,2-methylenedioxybenzene, 2-oxindole, 1,4-benzisoxazine, benzothiazole, quinoxaline, quinoline-N-oxide, isoquinoline-N-oxide, quinoxaline-N-oxide, quinazoline-N-oxide, benzoazine, phthalazine, 1,4-dioxo-1,2,3,4-tetrahydro-phthalazine, 2-oxo-1,2-dihydro-quinoline, 2,4-dioxo-1,4-dihydro-2H-benzo[d][1,3]oxazine, 2,5-dioxo-2,3,4,5-tetrahydro-1H-benzo[e][1,4]diazepine, or cinnoline.

When L is a 5 or 6-membered heteroaryl ring, preferred heteroaryl rings include pyridine, pyrimidine, imidazole, thiazole, thiazolidine, pyrrole, furan, thiophene, oxazole, or 1,2,4-triazole.

Either or both rings of the bicyclic aryl or bicyclic heteroaryl group may be fully unsaturated, partially saturated, or fully saturated. An oxo substituent on the bicyclic aryl or bicyclic heteroaryl moiety means that one of the carbon atoms has a carbonyl group. An thio substituent on the bicyclic aryl or bicyclic heteroaryl moiety means that one of the carbon atoms has a thiocarbonyl group.

When L is a 5 or 6-membered heteroaryl ring, it may be fully unsaturated, partially saturated, or fully saturated. The heteroaryl ring can be bound to A via carbon or nitrogen. An oxo substituent on the heteroaryl ring means that one of the carbon atoms has a carbonyl group. An thio substituent on the heteroaryl ring means that one of the carbon atoms has a thiocarbonyl group.

The alkyl portion of the alkyl, alkoxy, alkanoyloxy, alkoxymethyl, alkanoyloxymethyl, alkylsulphinyl, alkylsulphonyl, alkylsulfonamido, carboalkoxy, carboalkyl, carboxyalkyl, carboalkoxyalkyl, alkanoylamino, N-alkylcarbamoyl, and N,N-dialkylcarbamoyl, N-alkylaminoalkoxy, N,N-dialkylaminoalkoxy include both straight chain as well as branched carbon chains. The alkenyl portion of the alkenyl, alkenoyloxymethyl, alkenyloxy, alkenylsulfonamido, substituents include both straight chain as well as branched carbon chains and one or more sites of unsaturation and all possible configurational isomers. The alkynyl portion of the alkynyl, alkynoyloxymethyl, alkynylsulfonamido, alkynyloxy, substituents include both straight chain as well as branched carbon chains and one or more sites of unsaturation. Carboxy is defined as a —CO$_2$H radical. Carboalkoxy of 2–7 carbon atoms is defined as a —CO$_2$R" radical, where R" is an alkyl radical of 1–6 carbon atoms. Carboxyalkyl is defined as a HO$_2$C—R'"— radical where R'" is a divalent alkyl radical of 1–6 carbon atoms. Carboalkoxyalkyl is defined as a R"O$_2$C—R'"— radical where R'" is a divalent akyl radical and where R" and R'" together have 2–7 carbon atoms. Carboalkyl is defined as a —COR" radical, where R" is an alkyl radical of 1–6 carbon atoms. Alkanoyloxy is defined as a —OCOR" radical, where R" is an alkyl radical of 1–6 carbon atoms. Alkanoyloxymethyl is defined as R"CO$_2$CH$_2$— radical, where R" is an alkyl radical of 1–6 carbon atoms. Alkoxymethyl is defined as R"OCH$_2$— radical, where R" is an alkyl radical of 1–6 carbon atoms. Alkylsulphinyl is defined as R"SO— radical, where R" is an alkyl radical of 1–6 carbon atoms. Alkylsulphonyl is defined as R"SO$_2$— radical, where R" is an alkyl radical of 1–6 carbon atoms. Alkylsulfonamido, alkenylsulfonamido, alkynylsulfonamido are defined as R"SO$_2$NH— radical, where R" is an alkyl radical of 1–6 carbon atoms, an alkenyl radical of 2–6 carbon atoms, or an alkynyl radical of 2–6 carbon atoms, respectively. N-alkylcarbamoyl is defined as R"NHCO— radical, where R" is an alkyl radical of 1–6 carbon atoms. N,N-dialkylcarbamoyl is defined as R" R"NCO— radical, where R" is an alkyl radical of 1–6 carbon atoms, R' is an alkyl radical of 1–6 carbon atoms and R', and R" may be the same or different. When X is substituted, it is preferred that it is mono-, di-, or tri-substituted, with monosubstituted being most preferred. It is preferred that of the substituents R1 and R4, at least one is hydrogen and it is most preferred that both be hydrogen. It is also preferred that X is a phenyl ring, Z is —NH—, and n=0.

Het is a heterocycle, as defined above which may be optionally mono- or di-substituted with R$_6$ on carbon or nitrogen, optionally mono- or di-substituted on carbon with hydroxy, —N(R$_6$)$_2$, or —OR$_6$, optionally mono or di-substituted on carbon with with —(C(R$_6$)$_2$)$_s$OR$_6$ or —(C (R$_6$)$_2$)$_s$N(R$_6$)$_2$, and optionally mono or di-substituted on a saturated carbon with divalent —O— or —O(C(R$_6$)$_2$)$_s$O— (carbonyl and ketal groups, respectively); in some cases when Het is substituted with —O— (carbonyl), the carbonyl group can be hydrated. Het may be bonded to W when q=0 via a carbon atom on the heterocyclic ring, or when Het is a nitrogen containing heterocycle which also contains a saturated carbon-nitrogen bond, such heterocycle may be bonded to carbon, via the nitrogen when W is a bond. When q=0 and Het is a nitrogen containing heterocycle which also contains an unsaturated carbon-nitrogen bond, that nitrogen atom of the heterocycle may be bonded to carbon when W is a bond and the resulting heterocycle will bear a positive charge. When Het is substituted with R$_6$, such substitution may be on a ring carbon, or in the case of a nitrogen containing heterocycle, which also contains a saturated carbon-nitrogen, such nitrogen may be substituted with R$_6$ or in the case of a nitrogen containing heterocycle, which also contains an unsaturated carbon-nitrogen, such nitrogen may be substituted with R$_6$ in with case the heterocycle will bear a positive charge. Preferred heterocycles include pyridine, 2,6-disubstituted morpholine, 2,5-disubstituted thiomorpholine, 2-substituted imidazole, substituted thiazole, N-substituted imidazole, N-subsitituted 1,4-piperazine, N-subsitituted piperadine, and N-substituted pyrrolidine.

The compounds of Formula 3 may contain one or more asymmetric carbons atoms; in such cases, the compounds of Formula 3 include the individual diasteromers, the racemates, and the individual R and S entantiomers thereof. Some of the compound of this invention may contain one or more double bonds; in such cases, the compounds of this invention include each of the possible configurational isomers as well as mixtures of these isomers.

D. Cyanoquinolines of Formula 4, which are disclosed in U.S. patent application Ser. No. 09/162,289. These compounds can be prepared according to the methodology described in U.S. patent application Ser. No. 09/049,718, and U.S. patent application Ser. No. 09/162,289, which are hereby incorporated by reference. The structure of the EGFR kinase inhibitors of Formula 4 are as follows:

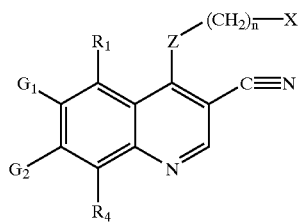

wherein:

X is cycloalkyl of 3 to 7 carbon atoms, which may be optionally substituted with one or more alkyl of 1 to 6 carbon atom groups; or is a pyridinyl, pyrimidinyl, or phenyl ring wherein the pyridinyl, pyrimidinyl, or phenyl ring may be optionally mono- di-, or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalky of 3–8 carbon atoms, aminoalkyl of 1–5 carbon atoms, N-alkylarninoalkyl of 2–9 carbon atoms, N,N-dialkylaminoalkyl of 3–10 carbon atoms, N-alkylaminoalkoxy of 2–9 carbon atoms, N,N-dialkylaminoalkoxy of 3–10 carbon atoms, mercapto, methylmercapto, and benzoylamino;

Z is —NH—, —O—, —S—, or —NR—;

R is alkyl of 1–6 carbon atoms, or carboalkyl of 2–7 carbon atoms;

G$_1$, G$_2$, R$_1$, and R$_4$ are each, independently, hydrogen, halogen, alkyl of 1–6 carbon atoms, alkenyl of 2–6 carbon atoms, alkynyl of 2–6 carbon atoms, alkenyloxy of 2–6 carbon atoms, alkynyloxy of 2–6 carbon atoms, hydroxymethyl, halomethyl, alkanoyloxy of 1–6 carbon atoms, alkenoyloxy of 3–8 carbon atoms, alkynoyloxy of 3–8 carbon atoms, alkanoyloxymethyl of 2–7 carbon atoms, alkenoyloxymethyl of 4–9 carbon atoms, alkynoyloxymethyl of 4–9 carbon atoms, alkoxymethyl of 2–7 carbon atoms, alkoxy of 1–6 carbon atoms, alkylthio of 1–6 carbon atoms, alkylsu=phinyl of 1–6 carbon atoms, alkylsulphonyl of 1–6 carbon atoms, alkylsulfonamido of 1–6 carbon atoms, alkenylsulfonamido of 2–6 carbon atoms, alkynylsulfonamido of 2–6 carbon atoms, hydroxy, trifluoromethyl, trifluoromethoxy, cyano, nitro, carboxy, carboalkoxy of 2–7 carbon atoms, carboalkyl of 2–7 carbon atoms, phenoxy, phenyl, thiophenoxy, benzyl, amino, hydroxyamino, alkoxyamino of 1–4 carbon atoms, alkylamino of 1–6 carbon atoms, dialkylamino of 2 to 12 carbon atoms, N-alkylcarbamoyl, N,N-dialkylcarbamoyl, N-alkyl-N-alkenylamino of 4 to 12 carbon atoms, N,N-dialkenylamino of 6–12 carbon atoms, phenylamino, benzylamino,

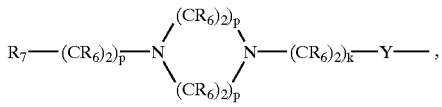

$R_8R_9$—CH—M—$(C(R_6)_2)_k$—Y—, $R_7$—$(C(R_6)_2)_g$—Y—,
$R_7$—$(C(R_6)_2)_p$—M—$(C(R_6)_2)_k$—Y—, or Het—$(C(R_6)_2)_q$—
W—$(C(R_6)_2)_k$—Y— with the proviso that either $G_1$ or $G_2$ or both $G_1$ and $G_2$ must be a radical selected from the group

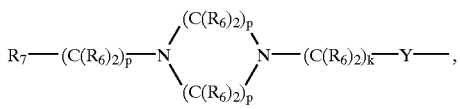

$R_8R_9$—CH—M—$(C(R_6)_2)_k$—Y—$R'_7$—$(C(R_6)_2)_g$—Y—,
$R_7$—$(C(R_6)_2)_p$—M—$(C(R_6)_2)_k$—Y—, Het—$(C(R_6)_2)_q$—W—
$(C(R_6)_2)_k$—Y—, or

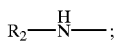

Y is a divalent radical selected from the group consisting of

—$(CH_2)_a$—, —O—, and

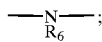

$R_7$ is —$NR_6R_6$, —J, —$OR_6$, —$N(R_6)_3^+$, or —$NR_6(OR_6)$;

$R'_7$ is —$NR_6(OR_6)$, —$N(R_6)_3^+$, alkenoxy of 1–6 carbon atoms, alkynoxy of 1–6 carbon atoms, N-alkyl-N-alkenylamino of 4 to 12 carbon atoms, N,N-dialkenylamino of 6–12 carbon atoms, N-alkyl-N-alkynylamino of 4 to 12 carbon atoms, N-alkenyl-N-alkynylamino of 4 to 12 carbon atoms, or N,N-dialkynylamino of 6–12 carbon atoms with the proviso that the alkenyl or alkynyl moiety is bound to a nitrogen or oxygen atom through a saturated carbon atom;

M is >$NR_6$, —O—, >N—$(C(R_6)_2)_p NR_6R_6$, or >N—$(C(R_6)_2)_p$—$OR_6$;

W is >$NR_6$, —O— or is a bond;

Het is a heterocycle selected from the group consisting of morpholine, thiomorpholine, thiomorpholine S-oxide, thiomorpholine S,S-dioxide, piperidine, pyrrolidine, aziridine, pyridine, imidazole, 1,2,3-triazole, 1,2,4-triazole, thiazole, thiazolidine, tetrazole, piperazine, furan, thiophene, tetrahydrothiophene, tetrahydrofuran, dioxane, 1,3-dioxolane tetrahydropyran, and

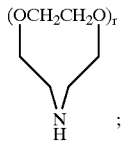

wherein the heterocycle is optionally mono- or di-substituted on carbon or nitrogen with $R_6$, optionally mono- or di-substituted on carbon with hydroxy, —$N(R_6)_2$, or —$OR_6$, optionally mono or di-substituted on carbon with the mono-valent radicals —$(C(R_6)_2)_s OR_6$ or —$(C(R_6)_2)_s N(R_6)_2$, or optionally mono or di-substituted on a saturated carbon with divalent radicals —O—or —$O(C(R_6)_2)_s$—O—;

$R_6$ is hydrogen, alkyl of 1–6 carbon atoms, alkenyl of 2–6 carbon atoms, alkynyl of 2–6 carbon atoms, cycloalkyl of 1–6 carbon atoms, carboalkyl of 2–7 carbon atoms, carboxyalkyl (2–7 carbon atoms), phenyl, or phenyl optionally substituted with one or more halogen, alkoxy of 1–6 carbon atoms, trifluoromethyl, amino, alkylamino of 1–3 carbon atoms, dialkylamino of 2–6 carbon atoms, nitro, cyano, azido, halomethyl, alkoxymethyl of 2–7 carbon atoms, alkanoyloxymethyl of 2–7 carbon atoms, alkylthio of 1–6 carbon atoms, hydroxy, carboxyl, carboalkoxy of 2–7 carbon atoms, phenoxy, phenyl, thiophenoxy, benzoyl, benzyl, phenylamino, benzylamino, alkanoylamino of 1–6 carbon atoms, or alkyl of 1–6 carbon atoms;

$R_2$, is selected from the group consisting of

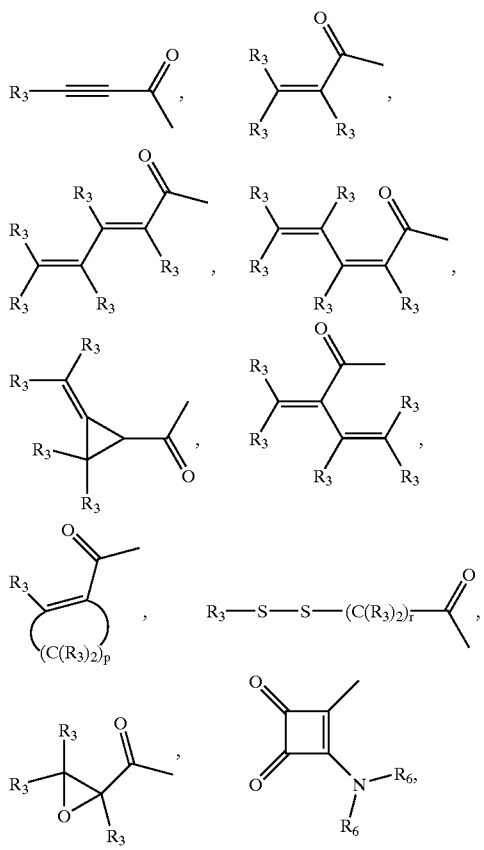

-continued

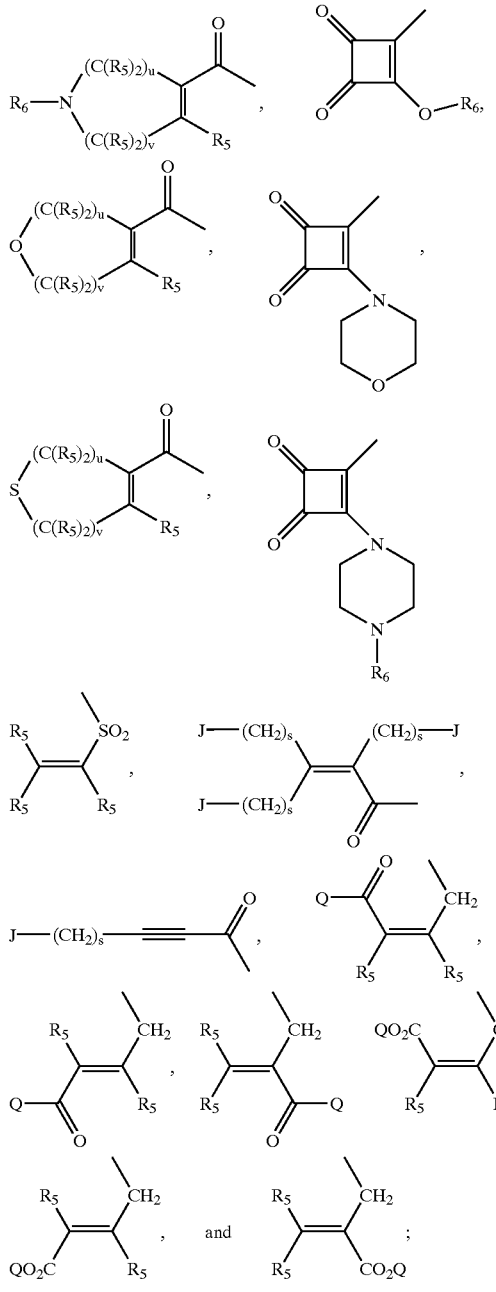

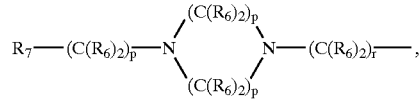

R'₇—(C(R₆)₂)ₛ—, R₇—(C(R₆)₂)ₚ—M—(C(R₆)₂)ᵣ, R₈R₉—CH—
M—(C(R₆)₂)ᵣ—, or Het—(C(R₆)₂)ᵩ—W—(C(R₆)₂)ᵣ;

$R_5$ is independently hydrogen, alkyl of 1–6 carbon atoms, carboxy, carboalkoxy of 1–6 carbon atoms, phenyl, carboalkyl of 2–7 carbon atoms,

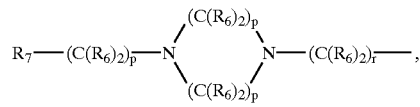

R₇—(C(R₆)₂)ₛ—, R₇—(C(R₆)₂)ₚ—M—(C(R₆)₂)ᵣ—, R₈R₉—CH—
M—(C(R₆)₂)ᵣ—, or Het—(C(R₆)₂)ᵩ—W—(C(R₆)₂)ᵣ—;

$R_8$, and $R_9$ are each, independently, —(C(R₆)₂)ᵣNR₆R₆, or —(C(R₆)₂)ᵣOR₆;

J is independently hydrogen, chlorine, fluorine, or bromine;

Q is alkyl of 1–6 carbon atoms or hydrogen;

a=0 or 1;

g=1–6;

k=0–4;

n is 0–1;

p=2–4;

q=0–4;

r=1–4;

s=1–6;

u=0–4 and v=0–4, wherein the sum of u+v is 2–4;

or a pharmaceutically acceptable salt thereof, provided that
when $R_6$ is alkenyl of 2–7 carbon atoms or alkynyl of 2–7 carbon atoms, such alkenyl or alkynyl moiety is bound to a nitrogen or oxygen atom through a saturated carbon atom;

and further provided that
when Y is —NR₆— and R₇ is —NR₆R₆, —N(R₆)₃⁺, or —NR₆(OR₆), then g=2–6;
when M is —O— and R₇ is —OR₆, then p=1–4;
when Y is —NR₆—, then k=2–4;
when Y is —O— and M or W is —O—, then k=1–4
when W is not a bond with Het bonded through a nitrogen atom, then q=2–4
and when W is a bond with Het bonded through a nitrogen atom and Y is —O— or —NR₆—, then k=2–4.

With respect to the cyanoquinolines of Formula 4, the pharmaceutically acceptable salts are those derived from such organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

The alkyl portion of the alkyl, alkoxy, alkanoyloxy, alkoxymethyl, alkanoyloxymethyl, alkylsulphinyl, alkylsulphonyl, aminoalkyl, N-alkylaminoalkyl, N,N-dialkylaminoalkyl, N-alkylaminoalkoxy, N,N-dialkylaminoalkoxy, alkylsulfonamido, carboalkoxy, $R_3$ is independently hydrogen, alkyl of 1–6 carbon atoms, carboxy, carboalkoxy of 1–6 carbon atoms, phenyl, carboalkyl of 2–7 carbon atoms,

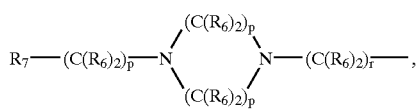

R₇—(C(R₆)₂)ₛ—, R₇—(C(R₆)₂)ₚ—M—(C(R₆)₂)ᵣ—, R₈R₉—CH—
M—(C(R₆)₂)ᵣ—, or Het—(C(R₆)₂)ᵩ—W—(C(R₆)₂)ᵣ—;

with the proviso that at least one of the $R_3$ groups is selected from the group carboalkyl, carboxyalkyl, carboalkoxyalkyl, alkanoylamino, N-alkylcarbamoyl, and N,N-dialkylcarbamoyl substituents include both straight chain as well as branched carbon chains. The alkenyl portion of the alkenyl, alkenoyloxymethyl, alkenyloxy, alkenylsulfonamido, substituents include both straight chain as well as branched carbon chains and one or more sites of unsaturation and all possible configurational isomers. The alkynyl portion of the alkynyl, alkynoyloxymethyl, alkynylsulfonamido, alkynyloxy, substituents include both straight chain as well as branched carbon chains and one or more sites of unsaturation. Carboxy is defined as a —$CO_2H$ radical. Carboalkoxy of 2–7 carbon atoms is defined as a —$CO_2R''$ radical, where R" is an alkyl radical of 1–6 carbon atoms. Carboxyalkyl is defined as a $HO_2C$—R'"— radical where R'" is a divalent alkyl radical of 1–6 carbon atoms. Carboalkoxyalkyl is defined as a $R''O_2C$—R'"— radical where R'" is a divalent akyl radical and where R" and R'" together have 2–7 carbon atoms. Carboalkyl is defined as a —COR" radical, where R" is an alkyl radical of 1–6 carbon atoms. Alkanoyloxy is defined as a —OCOR" radical, where R" is an alkyl radical of 1–6 carbon atoms. Alkanoyloxymethyl is defined as $R''CO_2CH_2$— radical, where R" is an alkyl radical of 1–6 carbon atoms. Alkoxymethyl is defined as $R''OCH_2$— radical, where R" is an alkyl radical of 1–6 carbon atoms. Alkylsulphinyl is defined as R"SO— radical, where R"is an alkyl radical of 1–6 carbon atoms. Alkylsulphonyl is defined as $R''SO_2$— radical, where R" is an alkyl radical of 1–6 carbon atoms. Alkylsulfonamido, alkenylsulfonamido, alkynylsulfonamido are defined as $R''SO_2NH$— radical, where R" is an alkyl radical of 1–6 carbon atoms, an alkenyl radical of 2–6 carbon atoms, or an alkynyl radical of 2–6 carbon atoms, respectively. N-alkylcarbamoyl is defined as R"NHCO— radical, where R" is an alkyl radical of 1–6 carbon atoms. N,N-dialkylcarbamoyl is defined as R" R'NCO— radical, where R" is an alkyl radical of 1–6 carbon atoms, R'is an alkyl radical of 1–6 carbon atoms and R', and R" may be the same or different. When X is substituted, it is preferred that it is mono-, di-, or tri-substituted, with monosubstituted being most preferred. It is preferred that of the substituents R1 and R4, at least one is hydrogen and it is most preferred that both be hydrogen. It is also preferred that X is a phenyl ring, Z is —NH—, and n=0.

Het is a heterocycle, as defined above which may be optionally mono- or di-substituted with $R_6$ on carbon or nitrogen, optionally mono- or di-substituted on carbon with hydroxy, —$N(R_6)_2$, or —$OR_6$, optionally mono or di-substituted on carbon with with —$(C(R_6)_2)_sOR_6$ or —$(C(R_6)_2)_sN(R_6)_2$, and optionally mono or di-substituted on a saturated carbon with divalent radicals —O— or —$O(C(R_6)_2)_sO$— (carbonyl and ketal groups, respectively); in some cases when Het is substituted with —O— (carbonyl), the carbonyl group can be hydrated. Het may be bonded to W when q=0 via a carbon atom on the heterocyclic ring, or when Het is a nitrogen containing heterocycle which also contains a saturated carbon-nitrogen bond, such heterocycle may be bonded to carbon, via the nitrogen when W is a bond. When q=0 and Het is a nitrogen containing heterocycle which also contains an unsaturated carbon-nitrogen bond, that nitrogen atom of the heterocycle may be bonded to carbon when W is a bond and the resulting heterocycle will bear a positive charge. When Het is substituted with $R_6$, such substitution may be on a ring carbon, or in the case of a nitrogen containing heterocycle, which also contains a saturated carbon-nitrogen, such nitrogen may be substituted with $R_6$ or in the case of a nitrogen containing heterocycle, which also contains an unsaturated carbon-nitrogen, such nitrogen may be substituted with $R_6$ in with case the heterocycle will bear a positive charge. Preferred heterocycles include pyridine, 2,6-disubstituted morpholine, 2,5-disubstituted thiomorpholine, 2-substituted imidazole, substituted thiazole, thiazolidine, N-substituted imidazole, N-subsitituted 1,4-piperazine, N-subsitituted piperadine, dioxane, 1,3-dioxolane, and N-substituted pyrrolidine.

The compounds Formula 4 may contain one or more asymmetric carbons atoms; in such cases, the compounds of Formula 4 include the individual diasteromers, the racemates, and the individual R and S entantiomers thereof. Some of the compound of Formula 4 may contain one or more double bonds; in such cases, the compounds of Formula 4 include each of the possible configurational isomers as well as mixtures of these isomers.

E. Naphthyridines of Formula 5, which are disclosed in U.S. patent application Ser. No. 09/295,507. These compounds can be prepared according to the methodology described in U.S. patent application Ser. No. 09/295,507, which is hereby incorporated by reference. The structure of the EGFR kinase inhibitors of Formula 5 are as follows:

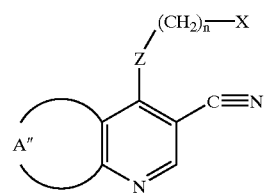

5 wherein:

X is cycloalkyl of 3 to 7 carbon atoms, which may be optionally substituted with one or more alkyl of 1 to 6 carbon atom groups; or X is pyridinyl, pyrimidinyl, or Ph; or X is a bicyclic aryl or bicyclic heteroaryl ring system of 8 to 12 atoms, where the bicyclic heteroaryl ring contains 1 to 4 heteroatoms selected from N, O, and S; wherein the bicyclic aryl or bicyclic heteroaryl ring may be optionally mono-, di-, tri-, or tetra-substituted with a substituent selected from the group consisting of halogen, oxo, thio, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalkyl of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 2–9 carbon atoms, N,N-dialkylaminoalkoxy of 3–10 carbon atoms, mercapto, methylmercapto, and benzoylamino; or X is the radical

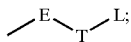

E is pyridinyl, pyrimidinyl, or Ph;
T is substituted on E at carbon and is

—NH(CH$_2$)$_m$—, —O(CH$_2$)$_m$—, —S(CH$_2$)$_m$—, —NR(CH$_2$)$_m$—,
—(CH$_2$)$_m$——(CH$_2$)$_m$NH—, —(CH$_2$)$_m$O—, —(CH$_2$)$_m$S—, or
—(CH$_2$)$_m$NR—;

L is a Ph; or
L is a 5- or 6-membered heteroaryl ring where the heteroaryl ring contains 1 to 3 heteroatoms selected from N, O, and S; wherein the heteroaryl ring may be optionally mono- or di-substituted with a substituent selected from the group consisting of halogen, oxo, thio, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalkyl of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 2–9 carbon atoms, N,N-dialkylaminoalkoxy of 3–10 carbon atoms, mercapto, methylmercapto, and benzoylamino;
Pyridinyl, pyrimidinyl, or Ph are pyridinyl, pyrimidinyl, or phenyl radicals, respectively, which may be optionally mono- di-, or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, benzoyl, amino, alkylamino of 1–6 carbon atoms, dialkylamino of 2 to 12 carbon atoms, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalkyl of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 2–9 carbon atoms, N,N-dialkylaminoalkoxy of 3–10 carbon atoms, mercapto, methylmercapto, and benzoylamino;
Z is —NH—, —O—, —S—, or —NR—;
R is alkyl of 1–6 carbon atoms, or carboalkyl of 2–7 carbon atoms;

A" is a divalent moiety selected from the group

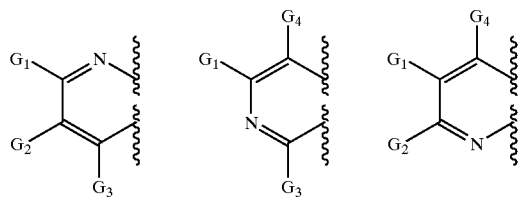

$G_1$, $G_2$, $G_3$, and $G_4$ are each, independently, hydrogen, halogen, alkyl of 1–6 carbon atoms, alkenyl of 2–6 carbon atoms, alkynyl of 2–6 carbon atoms, alkenyloxy of 2–6 carbon atoms, alkynyloxy of 2–6 carbon atoms, hydroxymethyl, halomethyl, alkanoyloxy of 2–6 carbon atoms, alkenoyloxy of 3–8 carbon atoms, alkynoyloxy of 3–8 carbon atoms, alkanoyloxymethyl of 2–7 carbon atoms, alkenoyloxymethyl of 4–9 carbon atoms, alkynoyloxymethyl of 4–9 carbon atoms, alkoxymethyl of 2–7 carbon atoms, alkoxy of 1–6 carbon atoms, alkylthio of 1–6 carbon atoms, alkylsulphinyl of 1–6 carbon atoms, alkylsulphonyl of 1–6 carbon atoms, alkylsulfonamido of 1–6 carbon atoms, alkenylsulfonamido of 2–6 carbon atoms, alkynylsulfonamido of 2–6 carbon atoms, hydroxy, trifluoromethyl, trifluoromethoxy, cyano, nitro, carboxy, carboalkoxy of 2–7 carbon atoms, carboalkyl of 2–7 carbon atoms, phenoxy, phenyl, thiophenoxy, benzyl, amino, hydroxyamino, alkoxyamino of 1–4 carbon atoms, alkylamino of 1–6 carbon atoms, dialkylamino of 2 to 12 carbon atoms, N-alkylcarbamoyl, N,N-dialkylcarbamoyl, N-alkyl-N-alkenylamino of 4 to 12 carbon atoms, N,N-dialkenylamino of 6–12 carbon atoms, phenylamino, benzylamino, R$_2$NH,

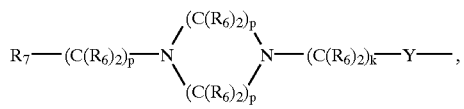

R$_8$R$_9$—CH—M—(C(R$_6$)$_2$)$_k$—Y—, R$_7$—(C(R$_6$)$_2$)$_g$—Y—,
R$_7$—(C(R$_6$)$_2$)$_p$—M—(C(R$_6$)$_2$)$_k$—Y—, Het—(C(R$_6$)$_2$)$_q$—W—(C(R$_6$)$_2$)$_k$—Y—, with the proviso that $G_3$ and $G_4$ are not R$_2$NH;
Y is a divalent radical selected from the group consisting of —S—, —(CH$_2$)$_a$—, —O—, and

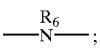

R$_7$ is —NR$_6$R$_6$, —OR$_6$, —J, —N(R$_6$)$_3$$^+$, or —NR$_6$(OR$_6$);
M is >NR$_6$, —O—, >N—(C(R$_6$)$_2$)$_p$NR$_6$R$_6$, or >N—(C(R$_6$)$_2$)$_p$—OR$_6$;
W is >NR$_6$, —O— or is a bond;
Het is a heterocyclic radical selected from the group consisting of morpholine, thiomorpholine, thiomorpholine S-oxide, thiomorpholine S,S-dioxide, piperidine, pyrrolidine, aziridine, pyridine, imidazole, 1,2,3-triazole, 1,2,4-triazole, thiazole, thiazolidine, tetrazole, piperazine, furan, thiophene, tetrahydrothiophene, tetrahydrofuran, dioxane, 1,3-dioxolane tetrahydropyran, and (OCH₂CH₂O)ᵣ attached to a piperidine-like NH ring;

which may be optionally mono- or di-substituted on carbon with $R_6$, hydroxy,

—N(R₆)₂, —OR₆—(C(R₆)₂)ₛOR₆ or —(C(R₆)₂)ₛN(R₆)₂;

optionally mono-substituted on nitrogen with $R_6$; and optionally mono or di-substituted on a saturated carbon with divalent radicals —O— or —O(C(R₆)₂)ₛO—;

$R_6$ is hydrogen, alkyl of 1–6 carbon atoms, alkenyl of 2–6 carbon atoms, alkynyl of 2–6 carbon atoms, cycloalkyl of 1–6 carbon atoms, carboalkyl of 2–7 carbon atoms, carboxyalkyl 2–7 carbon atoms, phenyl, or phenyl optionally substituted with one or more halogen, alkoxy of 1–6 carbon atoms, trifluoromethyl, amino, alkylamino of 1–3 carbon atoms, dialkylamino of 2–6 carbon atoms, nitro, cyano, azido, halomethyl, alkoxymethyl of 2–7 carbon atoms, alkanoyloxymethyl of 2–7 carbon atoms, alkylthio of 1–6 carbon atoms, hydroxy, carboxyl, carboalkoxy of 2–7 carbon atoms, phenoxy, phenyl, thiophenoxy, benzoyl, benzyl, phenylamino, benzylamino, alkanoylamino of 1–6 carbon atoms, or alkyl of 1–6 carbon atoms; with the proviso that the alkenyl or alkynyl moiety is bound to a nitrogen or oxygen atom through a saturated carbon atom;

$R_2$, is selected from the group consisting of

[chemical structures]

$R_3$ is hydrogen, alkyl of 1–6 carbon atoms, carboxy, carboalkoxy of 1–6 carbon atoms, phenyl, carboalkyl of 2–7 carbon atoms,

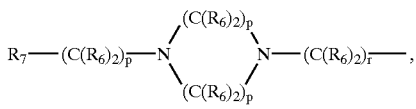

$R_7$—$(C(R_6)_2)_{\overline{s}}$—, $R_7$—$(C(R_6)_2)_p$—M—$(C(R_6)_2)_r$—, $R_8R_9$—CH—M—$(C(R_6)_2)_r$—, or Het—$(C(R_6)_2)_q$—W—$(C(R_6)_2)_r$—;

$R_5$ is hydrogen, alkyl of 1–6 carbon atoms, carboxy, carboalkoxy of 1–6 carbon atoms, phenyl, carboalkyl of 2–7 carbon atoms,

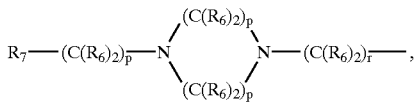

$R_7$—$(C(R_6)_2)_{\overline{s}}$—, $R_7(C(R_6)_2)_p$—M—$(C(R_6)_2)_r$—, $R_8R_9$—CH—M—$(C(R_6)_2)_r$—, or Het—$(C(R_6)_2)_q$—W—$(C(R_6)_2)_r$—;

$R_8$, and $R_9$ are each, independently, —$(C(R_6)_2)_r$NR$_6$R$_6$, or —$(C(R_6)_2)_r$OR$_6$;

J is independently hydrogen, chlorine, fluorine, or bromine;

Q is alkyl of 1–6 carbon atoms or hydrogen;

a=0–1;

g=1–6;

k=0–4;

n is 0–1;

m is 0–3;

p=2–4;

q=0–4;

r=1–4;

s=1–6;

u=0–4 and v=0–4, wherein the sum of u+v is 2–4;

or a pharmaceutically acceptable salt thereof, provided that
  when $R_6$ is alkenyl of 2–7 carbon atoms or alkynyl of 2–7 carbon atoms, such alkenyl or alkynyl moiety is bound to a nitrogen or oxygen atom through a saturated carbon atom;

and provided that
  when $R_3$ is bound to sulfur, it cannot be hydrogen, carboxy, carboalkoxy, or carboalkyl;

and provided that
  when Y is —NR$_6$— and $R_7$ is —NR$_6$R$_6$, —N(R$_6$)$_3^+$, or —NR$_6$(OR$_6$), then g=2–6;
  when M is —O— and $R_7$ is —OR$_6$ then p=1–4;
  when Y is —NR$_6$— then k=2–4;
  when Y is —O— and M or W is —O— then k=1–4
  when W is not a bond with Het bonded through a nitrogen atom then q=2–4
  and when W is a bond with Het bonded through a nitrogen atom and Y is —O— or —NR6- then k=2–4;
and finally provided that
  when A″ is the moiety

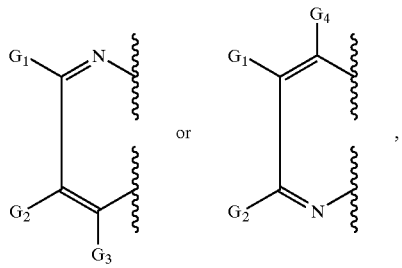

n=0,

Z is NH, $G_1$ is hydrogen, halogen, alkyl, alkoxy, hydroxy, alkanoyloxy of 2–6 carbon atoms, or phenoxy, and $G_2$ is hydrogen, halogen, alkyl, hydroxy, carboxyalkyl, carboalkoxyalkyl, hydroxyalkyl, alkoxy,halomethyl, carboxyl, carboalkoxy, alkanoylamino, or alkenoylamino, then X can not be a pyridinyl, pyrimidinyl, or phenyl ring that is substituted with a hydroxy or alkoxy group.

With respect to the naphthyridines of Formula 5, The pharmaceutically acceptable salts are those derived from such organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

Preferred bicyclic aryl or bicyclic heteroaryl ring systems include naphthalene, 1,2,3,4-tetrahydronaphthalene, tetralin, indane, 1-oxo-indane, 1,2,3,4-tetrahydroquinoline, naphthyridine, benzofuran, 3-oxo-1,3-dihydro-isobenzofuran, benzothiaphene, 1,1-dioxo-benzothiaphene, indole, 2,3-dihydroindole, 1,3-dioxo-2,3-dihydro-1H-isoindole, benzotriazole, 1H-indazole, indoline, benzopyrazole, 1,3-benzodioxole, benzooxazole, purine, phthalimide, coumarin, chromone, quinoline, terahydroquinoline, isoquinoline, benzimidazole, quinazoline, pyrido[2,3-b]pyridine, pyrido[3,4-b]pyrazine, pyrido[3,2-c]pyridazine, pyrido[3,4-b]pyridine, 1H-pyrazole[3,4-d]pyrimidine, 1,4-benzodioxane, pteridine, 2(1H)-quinolone, 1(2H)isoquinolone, 2-oxo-2,3-dihydro-benzthiazole, 1,2-methylenedioxybenzene, 2-oxindole, 1,4-benzisoxazine, benzothiazole, quinoxaline, quinoline-N-oxide, isoquinoline-N-oxide, quinoxaline-N-oxide, quinazoline-N-oxide, benzoazine, phthalazine, 1,4-dioxo-1,2,3,4-tetrahydro-phthalazine, 2-oxo-1,2-dihydro-quinoline, 2,4-dioxo-1,4-dihydro-2H-benzo[d][1,3]oxazine, 2,5-dioxo-2,3,4,5-tetrahydro-1H-benzo[e][1,4]diazepine, or cinnoline.

When L is a 5 or 6-membered heteroaryl ring, preferred heteroaryl rings include pyridine, pyrimidine, imidazole, thiazole, thiazolidine, pyrrole, furan, thiophene, oxazole, or 1,2,4-triazole.

Either or both rings of the bicyclic aryl or bicyclic heteroaryl group may be fully unsaturated, partially saturated, or fully saturated. An oxo substituent on the bicyclic aryl or bicyclic heteroaryl moiety means that one of the carbon atoms has a carbonyl group. A thio substituent on the bicyclic aryl or bicyclic heteroaryl moiety means that one of the carbon atoms has a thiocarbonyl group. When a compound of Formula 5 contains a moiety which contains a heteroaryl ring, such heteroaryl ring does not contain O—O, S—S, or S—O bonds in the ring.

When L is a 5 or 6-membered heteroaryl ring, it may be fully unsaturated, partially saturated, or fully saturated. The heteroaryl ring can be bound to T via carbon or nitrogen. An oxo substituent on the heteroaryl ring means that one of the carbon atoms has a carbonyl group. A thio substituent on the heteroaryl ring means that one of the carbon atoms has a thiocarbonyl group.

The alkyl portion of the alkyl, alkoxy, alkanoyloxy, alkoxymethyl, alkanoyloxymethyl, alkylsulphinyl, alkylsulphonyl, alkylsulfonamido, carboalkoxy, carboalkyl, carboxyalkyl, carboalkoxyalkyl, alkanoylamino, N-alkylcarbamoyl, and N,N-dialkylcarbamoyl, N-alkylaminoalkoxy, N,N-dialkylaminoalkoxy include both straight chain as well as branched carbon chains. The alkenyl portion of the alkenyl, alkenoyloxymethyl, alkenyloxy, alkenylsulfonamido, substituents include both straight chain as well as branched carbon chains and one or more sites of unsaturation and all possible configurational isomers. The alkynyl portion of the alkynyl, alkynoyloxymethyl, alkynylsulfonamido, alkynyloxy, substituents include both straight chain as well as branched carbon chains and one or more sites of unsaturation. Carboxy is defined as a —$CO_2H$ radical. Carboalkoxy of 2–7 carbon atoms is defined as a —$CO_2R"$— radical, where R" is an alkyl radical of 1–6 carbon atoms. Carboxyalkyl is defined as a $HO_2C$—R'"— radical where R'" is a divalent alkyl radical of 1–6 carbon atoms. Carboalkoxyalkyl is defined as a $R"O_2C$—R'"— radical where R'" is a divalent akyl radical and where R" and R'" together have 2–7 carbon atoms. Carboalkyl is defined as a —COR" radical, where R" is an alkyl radical of 1–6 carbon atoms. Alkanoyloxy is defined as a —OCOR" radical, where R" is an alkyl radical of 1–6 carbon atoms. Alkanoyloxymethyl is defined as $R"CO_2CH_2$— radical, where R" is an alkyl radical of 1–6 carbon atoms. Alkoxymethyl is defined as $R"OCH_2$— radical, where R" is an alkyl radical of 1–6 carbon atoms. Alkylsulphinyl is defined as R"SO— radical, where R" is an alkyl radical of 1–6 carbon atoms. Alkylsulphonyl is defined as $R"SO_2$— radical, where R" is an alkyl radical of 1–6 carbon atoms. Alkylsulfonamido, alkenylsulfonamido, alkynylsulfonamido are defined as $R"SO_2NH$— radical, where R" is an alkyl radical of 1–6 carbon atoms, an alkenyl radical of 2–6 carbon atoms, or an alkynyl radical of 2–6 carbon atoms, respectively. N-alkylcarbamoyl is defined as R"NHCO— radical, where R" is an alkyl radical of 1–6 carbon atoms. N,N-dialkylcarbamoyl is defined as R" R'NCO— radical, where R" is an alkyl radical of 1–6 carbon atoms, R' is an alkyl radical of 1–6 carbon atoms and R', and R" may be the same or different. When X is substituted, it is preferred that it is mono-, di-, or tri-substituted, with mono- and di-substituted being most preferred. It is preferred that of the substituents $G_3$ and $G_4$, at least one is hydrogen and it is most preferred that both be hydrogen. It is also preferred that X is a phenyl ring, Z is —NH—, and n=0.

Het is a heterocycle, as defined above which may be optionally mono- or di-substituted on carbon with $R_6$, optionally mono-substituted on nitrogen with $R_6$, optionally mono- or di-substituted on carbon with hydroxy, —$N(R_6)_2$, or —$OR_6$, optionally mono or di-substituted on carbon with —$(C(R_6)_2)_sOR_6$ or —$(C(R_6)_2)_sN(R_6)_2$, and optionally mono or di-substituted on a saturated carbon with divalent —O— or —$O(C(R_6)_2)_sO$— (carbonyl and ketal groups, respectively); in some cases when Het is substituted with —O— (carbonyl), the carbonyl group can be hydrated. Het may be bonded to W when q=0 via a carbon atom on the heterocyclic ring, or when Het is a nitrogen containing heterocycle which also contains a saturated carbon-nitrogen bond, such heterocycle may be bonded to carbon, via the nitrogen when W is a bond. When q=0 and Het is a nitrogen containing heterocycle which also contains an unsaturated carbon-nitrogen bond, that nitrogen atom of the heterocycle may be bonded to carbon when W is a bond and the resulting heterocycle will bear a positive charge. When Het is substituted with $R_6$, such substitution may be on a ring carbon, or in the case of a nitrogen containing heterocycle, which also contains a saturated carbon-nitrogen, such nitrogen may be substituted with $R_6$ or in the case of a nitrogen containing heterocycle, which also contains an unsaturated carbon-nitrogen, such nitrogen may be substituted with $R_6$ in with case the heterocycle will bear a positive charge. Preferred heterocycles include pyridine, 2,6-disubstituted morpholine, 2,5-disubstituted thiomorpholine, 2-substituted imidazole, substituted thiazole, N-substituted imidazole, N-subsitituted 1,4-piperazine, N-subsitituted piperadine, and N-substituted pyrrolidine.

The compounds of Formula 5 may contain one or more asymmetric carbon atoms; in such cases, the compounds of Formula 5 include the individual diasteromers, the racemates, and the individual R and S entantiomers thereof. Some of the compound of Formula 5 may contain one or more double bonds; in such cases, the compounds of Formula 5 include each of the possible configurational isomers as well as mixtures of these isomers. When a compound of Formula 5 contains a moiety containing the same substituent more than once (for example, when $R_7$ is —$NR_6R_6$), each substituent ($R_6$, in this example) may be the same or different.

F. Phenylamino quinazolines disclosed in WO 97/38983; 4-anilino quinolines disclosed in WO 96109294 and WO 98/13350; quinolines disclosed in U.S. Pat. No. 5,480,833, WO 98/02434, and WO 98/02438; quinazolines disclosed in EP 520722, EP 566226, WO 96/09294, WO 95/24190, WO 95/21613, WO 95/15758, EP 602851, EP 635498, WO 95/19774, WO 95/19970, EP 635507, WO 95/157581, WO 95/23141, WO 96/33977, WO 96/33978, WO 96/33979, WO 96/33980, WO 96/33981; tricyclic EGFR inhibitors disclosed in WO 95/19970; pyrrolopyrimidines disclosed in EP 682027; benzylidine-1,3-dihydro-indol-2-ones disclosed in WO 99/10325; tricyclic quinoxalines disclosed in WO 99/07701; pyrrolo[2,3d]pyrimidines disclosed in WO 98/41525; 2-pyrimidineamines disclosed in WO 98/18782 and WO 98/11095; 2-anilinopyrimidines disclosed in WO 97/19065; heterocyclic ring fused pyrimidines disclosed in WO 96/40142; benzylidine and cinnamylidine-malononitriles disclosed in EP 614661; 4-heterocyclyl-substituted quinazolines disclosed in U.S. Pat. No. 5,736,534; (4-substituted phenylamino) quinazolines disclosed in U.S. Pat. No. 5,747,498;

The ability of a combination of an NSAID and EGFR kinase inhibitor to treat or inhibit colonic polyps was demonstrated in an in vivo standard pharmacological test procedure as described below, using sulindac as a representative NSAID and N-[4-[(3-bromophenyl)amino]-6-quinazolinyl]-2-butynamide (a member of the EGFR kinase inhibitors of Formula 1) and (4-dimethylamino-but-2-enoic acid [4-(3-chloro-4-fluoro-phenylamino)-3-cyano-7-ethoxy-quinolin-6-yl]-amide (a member of the EGFR kinase inhibitors of Formula 2) as a representative EGFR kinase inhibitors. The preparation and activity of N-[4-[(3-bromophenyl)amino]-6-quinazolinyl]-2-butynamide as an EGFR kinase inhibitor are described in U.S. Pat. No. 5,760,041. The preparation and activity of (4-dimethylamino-but-2-enoic acid [4-(3-chloro-4-fluoro-phenylamino)-3-cyano-7-ethoxy-quinolin-6-yl]-amide as an EGFR kinase inhibitor are described in U.S. Pat. No. 6,002,008.

The procedure described below emulates familial adenomatous polyps (FAP) in humans using the Min mouse (C57BL/6J-Min/+), which is a strain which has lost both copies of the APC gene. These animals develop multiple intestinal polyps (adenomas) that ultimately progress to form adenocarcinomas. The polyps that develop in Min mice express EGFR and have activated COX-2. NSAID's such as sulindac and etodoloc can reduce (but not eradicate) intestinal polyp formulation in these animals indicating that COX-2 and the ultimate production of PG's is likely responsible for these effects. The following briefly describes the procedure used and the results obtained in this standard pharmacological test procedure.

Test animals were divided into four treatment groups: Group I, control; Group II, N-[4-[(3-bromophenyl)amino]-6-quinazolinyl]-2-butynamide; Group III, sulindac; and Group IV, combination of sulindac and N-[4-[(3-bromophenyl)amino]-6-quinazolinyl]-2-butynamide (hereinafter referred to as the NSAID/EGFR kinase inhibitor combination). The test compound was blended with a standard murine chow and animals were given ad libitum access to the food, in quantities corresponding to the following approximate daily dosages: Group II—40 mg/kg/day N-[4-[(3-bromophenyl)amino]-6-quinazolinyl]-2-butynamide; Group III—20 mg/kg/day sulindac; and Group IV—40 mg/kglday N-[4-[(3-bromophenyl)arnino]-6-quinazolinyl]-2-butynamide and 20 mglkg/day sulindac. The animals were treated for 60 days. The food was weighed once per week to determine consumption, and the animals also weighed weekly. On day 61, the animals were euthanized with $CO_2$ inhalation, and the entire intestinal tract from stomach to anus was removed. The intestinal tract was injected with Bouins fixative, and allowed to fix for several days. The intestinal tracts were then opened and the number of polyps counted. Statistical analysis was performed using the Student's t-Test; a p value of $\leq 0.05$ is considered statistically significant.

The following table summarizes the results that were obtained with N-[4-[(3-bromophenyl)amino]-6-quinazolinyl]-2-butynamide.

| Treatment Group | Number of Polyps | P value |
| --- | --- | --- |
| Group I | 32.3 ± 20.7 | |
| Group II | 15.6 ± 10.6 | <0.001 |
| Group III | 10.0 ± 6.6 | <0.001 |
| Group IV | 1.0 ± 0.96 | <0.001 |

The results obtained in this standard pharmacological test procedure showed that treatment with either sulindac or N-[4-[(3-bromophenyl)amino]-6-quinazolinyl]-2-butynamide alone reduced polyp numbers between 50 and 68 percent. The NSAID/EGFR kinase inhibitor combination reduced polyp numbers to virtually zero, clearly showing a synergistic interaction between the NSAID and the EGFR kinase inhibitor.

The above standard pharmacological test procedure was run again using lower dosages of sulindac in combination with an EGFR kinase inhibitor, as follows: Group I—control; Group II—40 mg/kg/day N-[4-[(3-bromophenyl)amino]-6-quinazolinyl]-2-butynamide and 10 mg/kg/day sulindac; and Group III—5 mg/kg/day N-[4-[(3-bromophenyl)amino]-6-quinazolinyl]-2-butynamide and 20 mg/kg/day sulindac. The following results were obtained.

| Treatment Group | Number of Polyps | P value |
| --- | --- | --- |
| Group I | 37.0 ± 27.9 | |
| Group II | 0.83 ± 1.33 | <0.001 |
| Group III | 0.07 ± 0.26 | <0.001 |

The above standard pharmacological test procedure was run again using (4-dimethylamino-but-2-enoic acid [4-(3-chloro-4-fluoro-phenylamino)-3-cyano-7-ethoxy-quinolin-6-yl]-amide as a representative EGFR kinase inhibitor, as follows. Test animals were divided into four treatment groups: Group I, control; Group II, (4-dimethylamino-but-2-enoic acid [4-(3-chloro-4-fluoro-phenylamino)-3-cyano-7-ethoxy-quinolin-6-yl]-amide Group III, sulindac; and Group IV, combination of sulindac and (4-dimethylamino-but-2-enoic acid [4-(3-chloro-4-fluoro-phenylamino)-3-cyano-7-ethoxy-quinolin 6-yl]-amide. The test compound was blended with a standard murine chow and animals were given ad libitum access to the food, in quantities corresponding to the following approximate daily dosages: Group II—20 mg/kg/(4-dimethylamino-but-2-enoic acid [4-(3-chloro-4-fluoro-phenylamino)-3-cyano-7-ethoxy-quinolin-6-yl]-amide, Group III—5 mg/kg/day sulindac; and Group IV—20 mg/kg/(4-dimethylamino-but-2-enoic acid [4-(3-chloro-4-fluoro-phenylamino)-3-cyano-7-ethoxy-quinolin-6-yl]-amide and 5 mg/kg/day sulindac. The animals were treated for 60 days. The food was weighed once per week to determnine consumption, and the animals also weighed weekly. On day 61, the animals were euthanized with $CO_2$ inhalation, and the entire intestinal tract from stomach to anus was removed. The intestinal tract was injected with Bouins fixative, and allowed to fix for several days. The intestinal tracts were then opened and the number of polyps counted. Statistical analysis was performed using the Students t-Test; a p value of $\leq 0.05$ is considered statistically significant.

The following table summarizes the results that were obtained.

| Treatment Group | Number of Polyps | P value |
| --- | --- | --- |
| Group I | 19.5 ± 14.1 | |
| Group II | 2.6 ± 1.6 | <0.001 |
| Group III | 20.6 ± 11.8 | <0.0001 |
| Group IV | 0.87 ± 1.1 | <0.001 |

The results obtained in this standard pharmacological test procedure showed that treatment with (4-dimethylamino-but-2-enoic acid [4-(3-chloro-4-fluoro-phenylamino)-3-cyano-7-ethoxy-quinolin-6-yl]-amide alone reduced polyp numbers 87 percent while sulindac alone at the 5 mg/kg dose did not reduce polyp numbers at all. The sulindac plus [4-(3-chloro-4-fluoro-phenylamino)-3-cyano-7-ethoxy-quinolin-6-yl]-amide combination reduced polyp numbers to virtually zero, again showing a synergistic interaction between the NSAID and an EGFR kinase inhibitor.

The results obtained in this standard pharmacological test procedure showed that the the NSAID/EGFR kinase inhibitor combination reduced the polyp numbers to virtually zero, at even lower doses of sulindac. Based on the results obtained in the standard pharmacological test procedure described above, the combinations of an NSAID with an EGFR kinase inhibitor is useful in treating or inhibiting colonic polyps and is also useful in treating or inhibiting colorectal cancer. It is also anticipated that the use of the combination of an NSAMD with an EGFR kinase inhibitor will significantly reduce the dosage of NSAID used to treat or inhibit colonic polyps or colorectal cancer, and thereby reduce the therapeutic liabilities associated with NSAID treatment.

The NSAID/EGFR kinase inhibitor combination of this invention may formulated neat or may be combined with one or more pharmaceutically acceptable carriers for administration. For example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solution or suspension containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of each active ingredient employed may vary depending on the particular compound employed, the mode of administration and the severity of the condition being treated. The projected daily dosage of the EGFR kinase inhibitor will depend on its potency. For the purpose of comparison N-[4-[(3-bromophenyl)amino]-6-quinazolinyl]-2-butynamide has an $IC_{50}$ of 2 nM in the test procedure which measured the inhibition of the phosphorylation of the tyrosine residue of a peptide substrate catalyzed by EGFR kinase. Similarly, the projected dosage of the NSAID used depends on the relative potency of the NSAID, compared for example to sulindac. Numerous methods for evaluating and comparing NSAID potency are known in the literature. Based on the results obtained in the standard pharmacogical test procedure utilizing the Min mouse, the projected oral daily dosage of the NSAID would be in the range of 2–30 mg/kg, and the projected daily dosage of the EGFR kinase inhibitor would be in the range of 1–50 mg/kg. This dosage regimen may be adjusted to provide the optimal therapeutic response. For example, several divided doses may be administered daily or the dose may be proportionally reduced as indicated by the exigencies of the therapeutic situation. The NSAID and the EGFR kinase inhibitor may also be administered as a combined dosage unit, or as separate components. When administered as separate components, each component may be administered at the same time, or at different times during the treatment period.

The NSAID/EGFR kinase inhibitor combination may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the NSAID/EGFR kinase inhibitor combination is preferred.

In some cases it may be desirable to administer the NSAID/EGFR kinase inhibitor combination directly to the airways in the form of an aerosol.

These NSAID/EGFR kinase inhibitor combination may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparation contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

What is claimed is:

1. A method of treating or inhibiting colonic polyps in a mammal in need thereof which comprises administering to said mammal effective synergistic amount of an NSAID and an EGFR kinase inhibitor, wherein the NSAID is selected from the group consisting of ibuprofen, sulindac, ketoporfen, fenoprofen, flurbiprofen, naproxen, tiaprofenic acid, suprofen, etodolac, carprofen, ketrolac, piprofen, indoprofen, celecoxib, rofecoxib, mobicox, and benoxaprofen, and wherein the EGFR kinase inhibitor is a compound of formula 2, having the structure

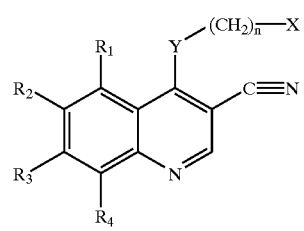

wherein:
X is cycloalkyl of 3 to 7 carbon atoms, which may be optionally substituted with one or more alkyl of 1 to 6 carbon atom groups; or is a pyridinyl, pyrimidinyl, or phenyl ring; wherein the pyridinyl, pyrimidinyl, or phenyl ring may be optionally mono- di-, or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, and benzoylamino;

n is 0–1;

Y is —NH—, —O—, —S—, or —NR—;

R is alkyl of 1–6 carbon atoms;

R$_1$, R$_2$, R$_3$, and R$_4$ are each, independently, hydrogen, halogen, alkyl of 1–6 carbon atoms, alkenyl of 2–6 carbon atoms, alkynyl of 2–6 carbon atoms, alkenyloxy of 2–6 carbon atoms, alkynyloxy of 2–6 carbon atoms, hydroxymethyl, halomethyl, alkanoyloxy of 1–6 carbon atoms, alkenoyloxy of 3–8 carbon atoms, alkynoyloxy of 3–8 carbon atoms, alkanoyloxymethyl of 2–7 carbon atoms, alkenoyloxymethyl of 4–9 carbon atoms, alkynoyloxymethyl of 4–9 carbon atoms, alkoxymethyl of 2–7 carbon atoms, alkoxy of 1–6 carbon atoms, alkylthio of 1–6 carbon atoms, alkylsulphinyl of 1–6 carbon atoms, alkylsulphonyl of 1–6 carbon atoms, alkylsulfonamido of 1–6 carbon atoms, alkenylsulfonamido of 2–6 carbon atoms, alkynylsulfonamido of 2–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzyl, amino, hydroxyamino, alkoxyamino of 1–4 carbon atoms, alkylamino of 1–6 carbon atoms, dialkylamino of 2 to 12 carbon atoms, aminoalkyl of 1–4 carbon atoms, N-alkylaminoalkyl of 2–7 carbon atoms, N,N-dialkylaminoalkyl of 3–14 carbon atoms, phenylamino, benzylamino,

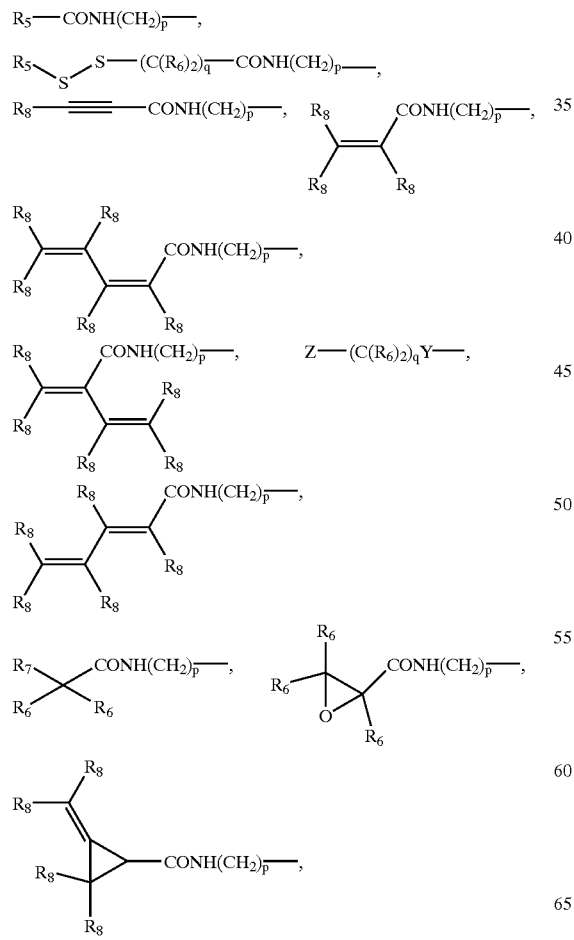

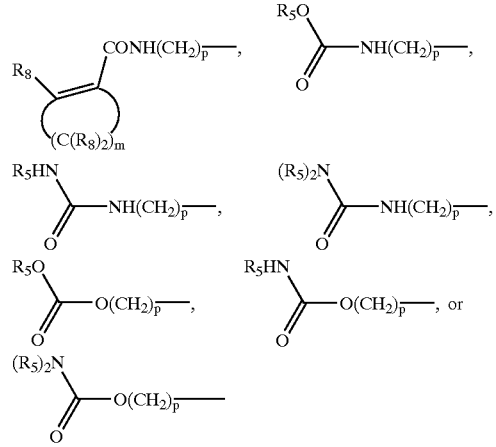

R$_5$ is alkyl of 1–6 carbon atoms, alkyl optionally substituted with one or more halogen atoms, phenyl, or phenyl optionally substituted with one or more halogen, alkoxy of 1–6 carbon atoms, trifluoromethyl, amino, nitro, cyano, or alkyl of 1–6 carbon atoms groups;

R$_6$ is hydrogen, alkyl of 1–6 carbon atoms, or alkenyl of 2–6 carbon atoms;

R$_7$ is chloro or bromo

R$_8$ is hydrogen, alkyl of 1–6 carbon atoms, aminoalkyl of 1–6 cabon atoms, N-alkylaminoalkyl of 2–9 carbon atoms, N,N-dialkylaminoalkyl of 3–12 carbon atoms, N-cycloalkylaminoalkyl of 4–12 carbon atoms, N-cycloalkyl-N-alkylaminoalkyl of 5–~carbon atoms, N,N-dicycloalkylaminoalkyl of 7–18 carbon atoms, morpholino-N-alkyl wherein the alkyl group is 1–6 carbon atoms, piperidino-N-alkyl wherein the alkyl group is 1–6 carbon atoms, N-alkyl-piperidino-N-alkyl wherein either alkyl group is 1–6 carbon atoms, azacycloalkyl-N-alkyl of 3–11 carbon atoms, hydroxyalkyl of 1–6 carbon atoms, alkoxyalkyl of 2–8 carbon atoms, carboxy, carboalkoxy of 1–6 carbon atoms, phenyl, carboalkyl of 2–7 carbon atoms, chloro, fluoro, or bromo;

Z is amino, hydroxy, alkoxy of 1–6 carbon atoms, alkylamino wherein the alkyl moiety is of 1–6 carbon atoms, dialkylamino wherein each of the alkyl moieties is of 1–6 carbon atoms, morpholino, piperazino, N-alkylpiperazino wherein the alkyl moiety is of 1–6 carbon atoms, or pyrrolidino;

m=1–4, q=1–3, and p=0–3;

any of the substituents R$_1$, R$_2$, R$_3$, or R$_4$ that are located on contiguous carbon atoms can together be the divalent radical —O—C(R$_8$)$_2$—O—;

or a pharmaceutically acceptable salt thereof with the proviso that when Y is —NH—, R$_1$, R$_2$, R$_3$, and R$_4$ are hydrogen, and n is 0, X is not 2-methylphenyl.

2. The method according to claim 1, wherein the EGFR kinase inhibitor irreversibly inhibits EGFR kinase.

3. The method according to claim 1, wherein the NSAID is sulindac.

4. The method according to claim 3, wherein the EGFR kinase inhibitor is (4-dimethylamino-but-2-enoic acid [4-(3-chloro-4-fluoro-phenylamino)-3-cyano-7-ethoxy-quinolin-6-yl]-amide or a pharmaceutically acceptable salt therof.

5. A method of treating or inhibiting colorectal cancer in a mammal in need thereof which comprises administering to said mammal an effective synergistic amount of an NSAID and an EGFR kinase inhibitor, wherein the NSAID is selected from the group consisting of ibuprofen, sulindac, ketoporfen, fenoprofen, flurbiprofen, naproxen, tiaprofenic acid, suprofen, etodolac, carprofen, ketrolac, piprofen, indoprofen, celecoxib, rofecoxib, mobicox, and benoxaprofen, and wherein the EGFR kinase inhibitor is a compound of formula 2, having the structure

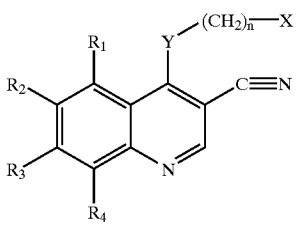
2 wherein:

X is cycloalkyl of 3 to 7 carbon atoms, which may be optionally substituted with one or more alkyl of 1 to 6 carbon atom groups; or is a pyridinyl, pyrimidinyl, or phenyl ring; wherein the pyridinyl, pyrimidinyl, or phenyl ring may be optionally mono- di-, or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, and benzoylamino;

n is 0–1;

Y is —NH—, —O—, —S—, or —NR—;

R is alkyl of 1–6 carbon atoms;

$R_1$, $R_2$, $R_3$, and $R_4$ are each, independently, hydrogen, halogen, alkyl of 1–6 carbon atoms, alkenyl of 2–6 carbon atoms, alkynyl of 2–6 carbon atoms, alkenyloxy of 2–6 carbon atoms, alkynyloxy of 2–6 carbon atoms, hydroxymethyl, halomethyl, alkanoyloxy of 1–6 carbon atoms, alkenoyloxy of 3–8 carbon atoms, alkynoyloxy of 3–8 carbon atoms, alkanoyloxymethyl of 2–7 carbon atoms, alkenoyloxymethyl of 4–9 carbon atoms, alkynoyloxymethyl of 4–9 carbon atoms, alkoxymethyl of 2–7 carbon atoms, alkoxy of 1–6 carbon atoms, alkylthio of 1–6 carbon atoms, alkylsulphinyl of 1–6 carbon atoms, alkylsulphonyl of 1–6 carbon atoms, alkylsulfonamido of 1–6 carbon atoms, alkenylsulfonamido of 2–6 carbon atoms, alkynylsulfonamido of 2–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzyl, amino, hydroxyamino, alkoxyamino of 1–4 carbon atoms, alkylamino of 1–6 carbon atoms, dialkylamino of 2 to 12 carbon atoms, aminoalkyl of 1–4 carbon atoms, N-alkylaminoalkyl of 2–7 carbon atoms, N,N-dialkylamninoalkyl of 3–14 carbon atoms, phenylamino, benzylamino,

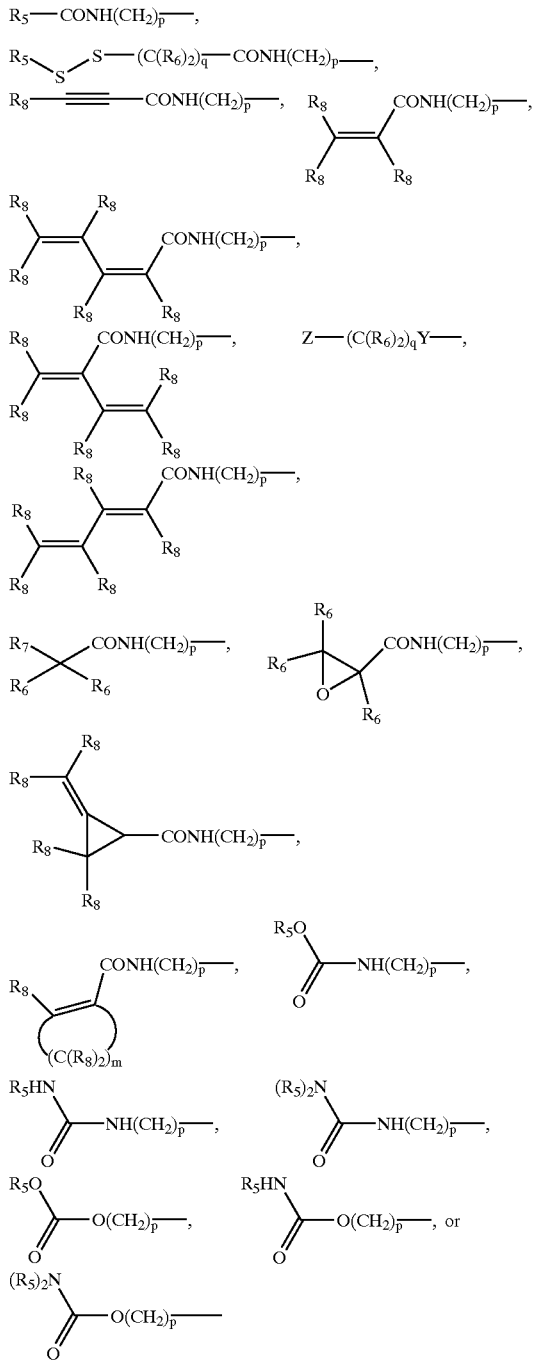

$R_5$ is alkyl of 1–6 carbon atoms, alkyl optionally substituted with one or more halogen atoms, phenyl, or phenyl optionally substituted with one or more halogen, alkoxy of 1–6 carbon atoms, trifluoromethyl, amino, nitro, cyano, or alkyl of 1–6 carbon atoms groups;

$R_6$ is hydrogen, alkyl of 1–6 carbon atoms, or alkenyl of 2–6 carbon atoms;

$R_7$ is chloro or bromo $R_8$ is hydrogen, alkyl of 1–6 carbon atoms, aminoalkyl of 1–6 cabon atoms, N-alkylaminoalkyl of 2–9 carbon atoms, N,N-dialkylaminoalkyl of 3–12 carbon atoms, N-cycloalkylaminoalkyl of 4–12 carbon atoms, N-cycloalkyl-N-alkylaminoalkyl of 5–18 carbon atoms, N,N-dicycloalkylaminoalkyl of 7–18 carbon atoms, morpholino-N-alkyl wherein the alkyl group is 1–6 carbon atoms, piperidino-N-alkyl wherein the alkyl group is 1–6 carbon atoms, N-alkyl-piperidino-N-alkyl wherein either alkyl group is 1–6 carbon atoms, azacycloalkyl-N-alkyl of 3–11 carbon atoms, hydroxyalkyl of 1–6 carbon atoms, alkoxyalkyl of 2–8 carbon atoms, carboxy, carboalkoxy of 1–6 carbon atoms, phenyl, carboalkyl of 2–7 carbon atoms, chloro, fluoro, or bromo;

Z is amino, hydroxy, alkoxy of 1–6 carbon atoms, alkylamino wherein the alkyl moiety is of 1–6 carbon atoms, dialkylamino wherein each of the alkyl moieties is of 1–6 carbon atoms, morpholino, piperazino, N-alkylpiperazino wherein the alkyl moiety is of 1–6 carbon atoms, or pyrrolidino;

m=1–4, q=1–3, and p=0–3;

any of the substituents $R_1$, $R_2$, $R_3$, or $R_4$ that are located on contiguous carbon atoms can together be the divalent radical —O—C($R_8$)$_2$—O—;

or a pharmaceutically acceptable salt thereof with the proviso that when Y is —NH—, $R_1$, $R_2$, $R_3$, and $R_4$ are hydrogen, and n is 0, X is not 2-methylphenyl.

6. The method according to claim 5, wherein the NSAID is sulindac.

7. The method according to claim 6, wherein the EGFR kinase inhibitor is (4-dimethylamino-but-2-enoic acid [4-(3-chloro-4-fluoro-phenylamino)-3-cyano-7-ethoxy-quinolin-6-yl]-amide or a pharmaceutically acceptable salt therof.

* * * * *